US012799149B2

(12) United States Patent
Gu

(10) Patent No.: US 12,799,149 B2
(45) Date of Patent: Nov. 17, 2026

(54) FLUORINATED BENZOYL ANTHRACYCLINE DERIVATIVES, AND PREPARATION AND APPLICATIONS OF SAME

(71) Applicant: Ye Gu, Wuhan City (CN)

(72) Inventor: Ye Gu, Wuhan City (CN)

( * ) Notice: Subject to any disclaimer, the term of this patent is extended or adjusted under 35 U.S.C. 154(b) by 0 days.

(21) Appl. No.: 19/195,772

(22) Filed: May 1, 2025

(65) Prior Publication Data

US 2026/0008804 A1 Jan. 8, 2026

(30) Foreign Application Priority Data

Jul. 8, 2024 (CN) ......................... 202410908701.9

(51) Int. Cl.
*C07H 15/252* (2006.01)
*A61K 31/704* (2006.01)

(52) U.S. Cl.
CPC ......... *C07H 15/252* (2013.01); *A61K 31/704* (2013.01)

(58) Field of Classification Search
CPC ........ C07H 15/252; A61K 31/704; A61P 9/06
See application file for complete search history.

(56) References Cited

U.S. PATENT DOCUMENTS 5,744,454 A * 4/1998 Suarato .................. A61P 25/28 536/6.4

OTHER PUBLICATIONS

"Ablation", Published Apr. 22, 2018, NCI Dictionary, 1 page, Retrieved from Internet <https://web.archive.org/web/20180422225521/https://www.cancer.gov/publications/dictionaries/cancer-terms/def/ablation> (Year: 2018).*

Neilan et al., Published Mar. 1, 2013, The American Journal of Cardiology, vol. 111, Issue 5, pp. 717-722 (Year: 2013).*

Martuszewski et al., Published Mar. 17, 2025, Journal of Clinical Medicine, vol. 14, Issue 6, pp. 1-32 (Year: 2025).*

Leiva et al., Published Jan. 26, 2023, Cardiology, vol. 148, Issue 4, pp. 324-334 (Year: 2023).*

Hermentin et al., Published Mar. 1, 1990, Bioconjugate Chemistry, vol. 1, Issue 2, pp. 100-107 (Year: 1990).*

Brown, N., "Bioisosterism in Medicinal Chemistry" in: Brown, N., Bioisoteres in Medicinal Chemistry (Weinheim, Wiley-VCH Verlag & Co. KGaA, 2012), pp. 3-14 (Year: 2012).*

Keum et al., Published May 21, 2024, Advanced Materials, vol. 36, Issue 32, pp. 1-33 (Year: 2024).*

* cited by examiner

*Primary Examiner* — Renee Claytor
*Assistant Examiner* — Jaret J Crews
(74) *Attorney, Agent, or Firm* — troutman pepper locke; Tim Tingkang Xia, Esq.

(57) ABSTRACT

The invention discloses a class of fluorobenzoyl anthracycline derivatives, and preparation method for preparing and applications of the same. The fluorobenzoyl anthracycline derivatives have chemical formula of

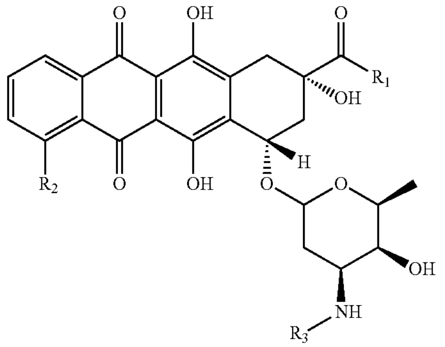

where $R_1$ is selected from the group consisting of —$CH_3$, —$CH_2OH$ and —O—$CH_3$ groups; $R_2$ is selected from the group consisting of —H, —OH and —O—CH3 groups; and $R_3$ is a trifluoromethyl-substituted benzoyl group or a trifluoromethylphenyl-substituted benzoyl group. The preparation method involves the derivatization of fluorobenzoyl groups on the amino group of anthracycline derivatives. These derivatives act as ablation media for chemical ablation of heterogeneous myocardial tissues, achieving effective myocardial damage with targeted localization and controllable damage characteristics.

6 Claims, 16 Drawing Sheets

LCMS Report

Exact Mass: 715.19

Integration Result

PDA Ch1 220nm

| Peak# | Ret. Time | Height | Height% | USP Width | Area | Area% |
|---|---|---|---|---|---|---|
| 1 | 0.297 | 7943 | 1.598 | 0.024 | 7216 | 1.882 |
| 2 | 0.350 | 14011 | 2.820 | 0.017 | 9136 | 2.383 |
| 3 | 0.447 | 474978 | 95.582 | 0.020 | 367026 | 95.735 |

PDA Ch2 254nm

| Peak# | Ret. Time | Height | Height% | USP Width | Area | Area% |
|---|---|---|---|---|---|---|
| 1 | 0.351 | 15946 | 3.803 | 0.017 | 10139 | 3.207 |
| 2 | 0.447 | 403387 | 96.197 | 0.020 | 306008 | 96.793 |

LCMS Report

Target

Method Info :Instrument: Shimadzu LC-20AD MSD:LCMS-2020
Column:HALO C18 3.0*30mm,2.7um
Mobile Phase:A:0.0375% TFA in H2O
Mobile Phase:B:0.01875% TFA in ACN Chromatogram MS Chromatogram

Integration Result

PDA Ch1 220nm

| Peak# | Ret. Time | Height | Height% | USP Width | Area | Area% |
|---|---|---|---|---|---|---|
| 1 | 1.476 | 24971 | 3.709 | 0.044 | 42314 | 3.630 |
| 2 | 1.700 | 2582 | 0.383 | 0.082 | 8002 | 0.687 |
| 3 | 1.846 | 2161 | 0.321 | 0.039 | 3222 | 0.276 |
| 4 | 2.530 | 642386 | 95.420 | 0.045 | 1109880 | 95.224 |
| 5 | 2.665 | 1120 | 0.166 | 0.056 | 2133 | 0.183 |

PDA Ch2 254nm

| Peak# | Ret. Time | Height | Height% | USP Width | Area | Area% |
|---|---|---|---|---|---|---|
| 1 | 1.476 | 27276 | 4.732 | 0.044 | 46283 | 4.606 |
| 2 | 2.530 | 549090 | 95.268 | 0.045 | 958605 | 95.394 |

Exact Mass: 850.21

LCMS Report

Exact Mass: 858.21

Integration Result

PDA Ch1 220nm

| Peak# | Ret. Time | Height | Height% | USP Width | Area | Area% |
|---|---|---|---|---|---|---|
| 1 | 0.526 | 363208 | 100.000 | 0.025 | 351705 | 100.000 |

PDA Ch2 254nm

| Peak# | Ret. Time | Height | Height% | USP Width | Area | Area% |
|---|---|---|---|---|---|---|
| 1 | 0.526 | 483885 | 100.000 | 0.025 | 469576 | 100.000 |

FLUORINATED BENZOYL ANTHRACYCLINE DERIVATIVES, AND PREPARATION AND APPLICATIONS OF SAME

CROSS-REFERENCE TO RELATED PATENT APPLICATION

This application claims priority to and the benefit of Chinese Patent Application Serial No. 202410908701.9, filed Jul. 8, 2024, which is incorporated herein in its entirety by reference.

FIELD OF THE INVENTION

This invention relates to the field of pharmaceutical compounds, and more particularly to a class of anthracene ring structure derivatives containing fluorinated benzoyl groups, preparations and applications of the same.

BACKGROUND OF THE INVENTION

In cardiac diseases, there exists a category of pathological myocardial abnormalities due to developmental anomalies and/or functional impairments, which can be life-threatening in severe cases. These heterogeneous myocardial abnormalities manifest in various forms in cardiac conditions. Structurally, hypertrophic cardiomyopathy (HCM) with severe left ventricular outflow tract obstruction (LVOTO) is a primary example, where patients suffer from circulatory disorders that can lead to death. In the field of electrophysiology, patients frequently experience various arrhythmias, such as atrial fibrillation or rapid ventricular rhythms, posing severe risks to their lives.

Over the past 30 years, technological advancements have led to the development of myocardial ablation techniques for treating heterogeneous myocardial conditions. These techniques include chemical ablation, such as alcohol septal ablation (ASA), and physical ablation methods, such as catheter-based radiofrequency ablation for arrhythmia treatment. Despite the implementation of these ablation techniques in disease treatment, numerous unresolved clinical issues remain. For instance, ASA procedures often result in severe and even fatal complications during or after surgery. Additionally, catheter-based radiofrequency ablation is ineffective in eliminating epicardial ectopic foci and fails to prevent the recurrence of persistent atrial fibrillation.

Taking HCM as an example, it has been established that LVOTO is closely associated with cardiovascular mortality. To reduce cardiovascular events, clinicians have developed alcohol ablation methods for hypertrophic myocardium, which have become a primary septal reduction technique. However, clinical practice has shown that ASA procedures frequently cause severe or even fatal complications, including complete heart block, early ventricular arrhythmias, coronary artery dissection, and accidental ethanol leakage leading to sudden death or remote myocardial infarction. To mitigate these severe complications, clinicians have continuously innovated by employing materials such as polyvinyl alcohol particles, microspheres, absorbable gelatin sponges, and septal coils to occlude blood vessels and induce necrosis of hypertrophic myocardial tissue. Additionally, novel catheter-based radiofrequency and cryoablation techniques have been explored. Surgeons have also been developing and refining surgical approaches. Unfortunately, the low clinical benefit-to-risk ratio has prevented the widespread adoption of these techniques.

Therefore, developing an effective myocardial ablation treatment for heterogeneous myocardial conditions is of significant importance and beneficial for saving the lives of cardiac disease patients, alleviating their suffering, and improving their quality of life.

SUMMARY OF THE INVENTION

This invention addresses the limitations of existing technology by providing a class of fluorobenzoyl anthracycline derivatives, along with their preparations and applications. These derivatives can serve as ablation media for heterogeneous myocardial ablation, achieving effective myocardial damage with targeted localization and controllable injury.

To achieve the foregoing objectives, the invention adopts the following technical solutions:

In a first aspect, the invention relates to a class of fluorobenzoyl anthracycline derivatives with a structure represented by formula (I):

Formula (I)

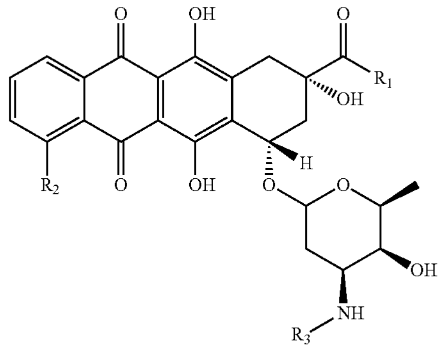

wherein $R_1$ is selected from the group consisting of —$CH_3$, —$CH_2OH$ and —O—$CH_3$ groups; $R_2$ is selected from the group consisting of —H, —OH and —O—$CH_3$ groups; $R_3$ is a trifluoromethyl-substituted benzoyl group or a trifluoromethylphenyl-substituted benzoyl group.

When $R_3$ is the trifluoromethyl-substituted benzoyl group, the structure of the formula (I) is:

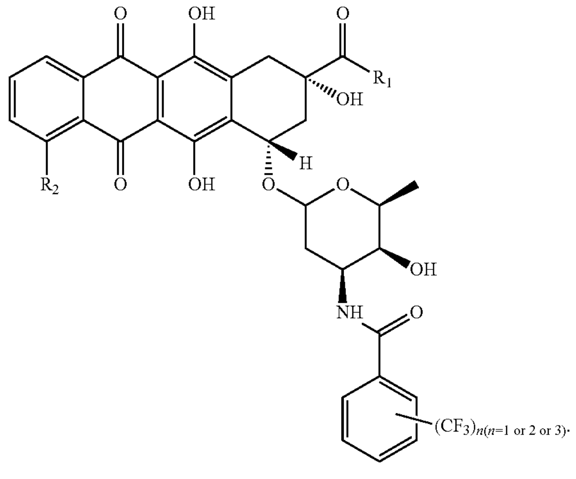

When $R_3$ is the trifluoromethylphenyl-substituted benzoyl group, the structure of the formula (I) is:

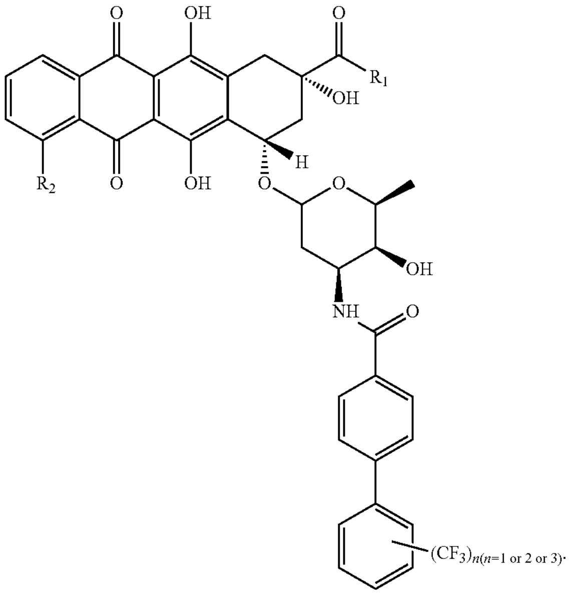

In one embodiment, the trifluoromethyl-substituted benzoyl group includes a mono-substituted, di-substituted, or tri-substituted trifluoromethyl group having the structures respectively shown as follows:

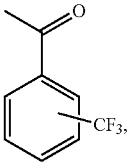
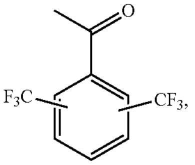
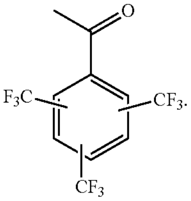

In one embodiment, the trifluoromethylphenyl-substituted benzoyl group includes a mono-substituted, di-substituted, or tri-substituted trifluoromethylphenyl group having the structures respectively shown as follows:

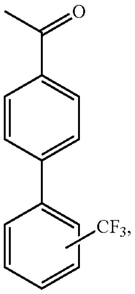
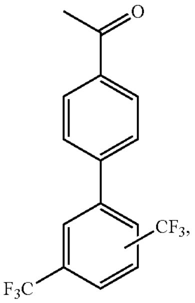
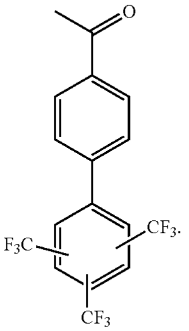

In one embodiment, the trifluoromethyl-substituted benzoyl group includes one or more of the followings specific structures:

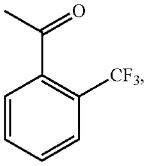
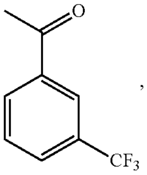
,
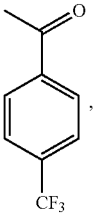
,

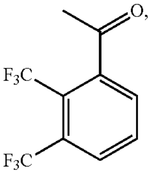
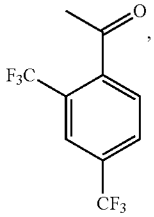
,
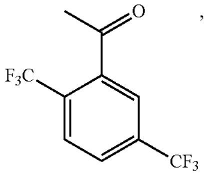
,

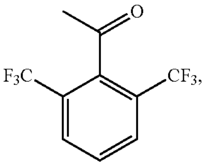
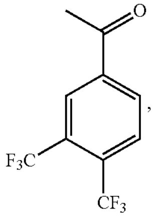
,

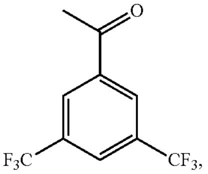
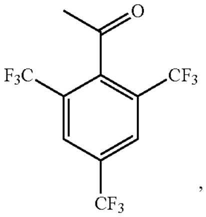
,

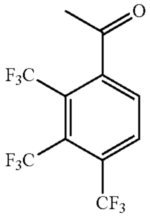
,
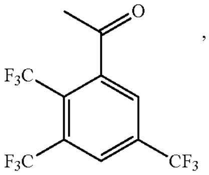
,

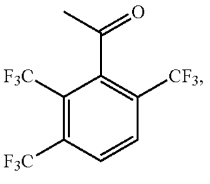
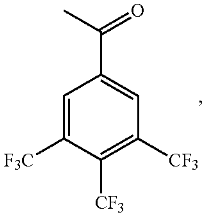
,

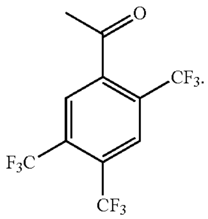

In one embodiment, the trifluoromethylphenyl-substituted benzoyl group specifically includes one or more of the followings specific structures:

-continued
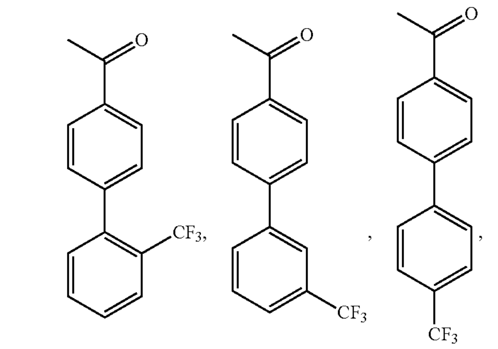
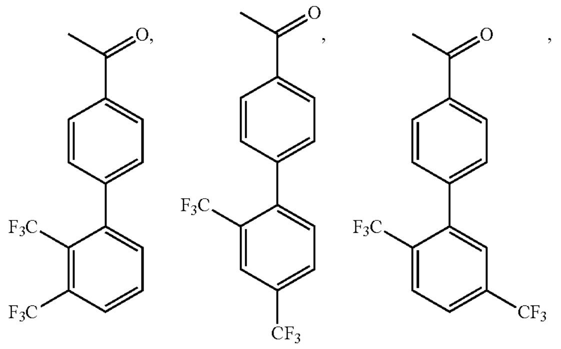
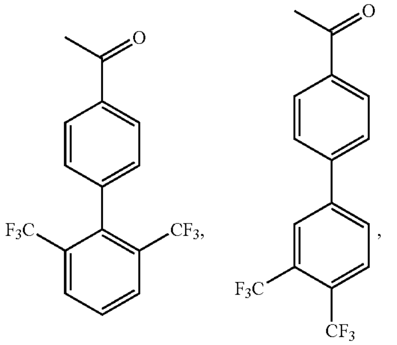
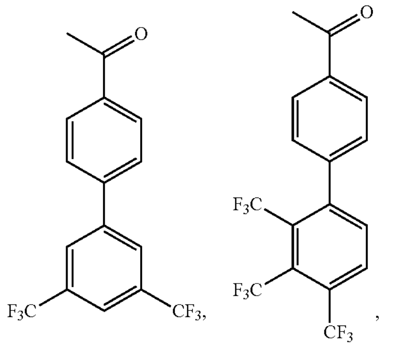
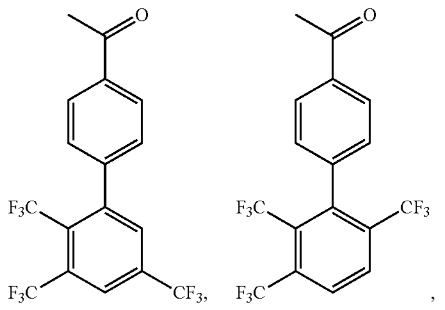
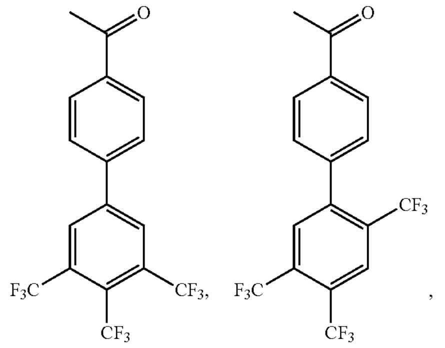
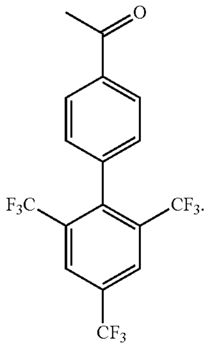
In one embodiment, the fluorobenzoyl anthracycline derivatives include, but are not limited to, the following compounds represented by Formula (II), Formula (III) and Formula (IV), respectively:
Formula (II)
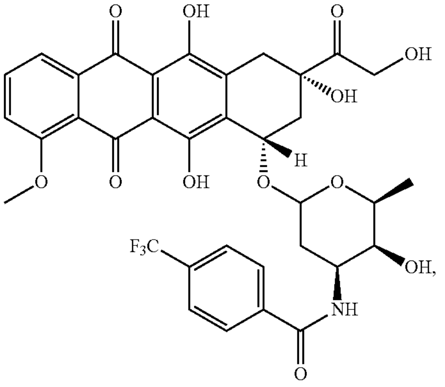

-continued

Formula (III)

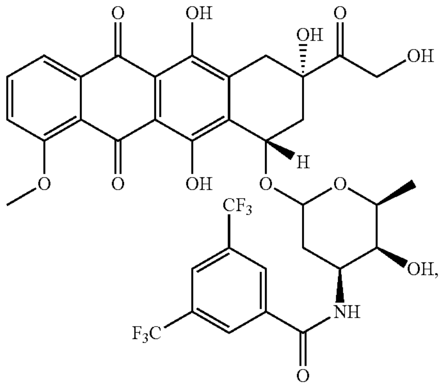

Formula (IV)

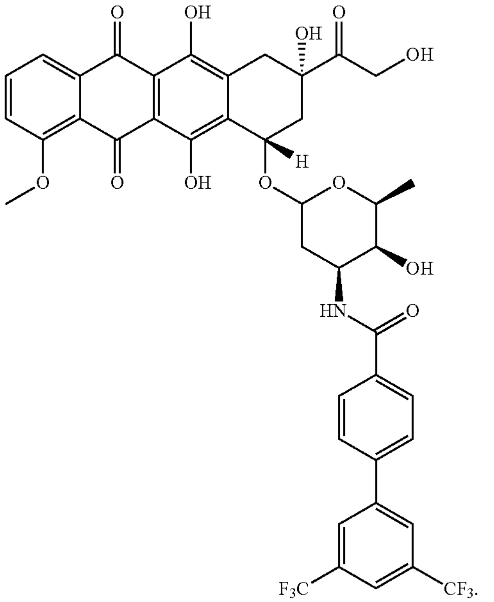 [SMILES: COc1cccc2c1C(=O)c1c(O)c3c(c(O)c1C2=O)C[C@@](O)(C(=O)CO)C[C@@H]3OC1C[C@H](NC(=O)c2ccc(-c3cc(C(F)(F)F)cc(C(F)(F)F)c3)cc2)[C@H](O)[C@H](C)O1]

In a second aspect, the invention relates to a method of preparing the fluorobenzoyl anthracycline derivatives as disclosed above. The synthesis route involves an anthracycline compound (represented by Formula (1)) or its hydrochloride reacting with a trifluoromethyl-substituted benzoyl chloride (represented by Formula (2)), or a trifluoromethylphenyl-substituted benzoyl chloride (represented by Formula (3)) via an amide reaction, to prepare the anthracene ring structure derivative containing a fluorinated benzoyl group.

Formula (1)

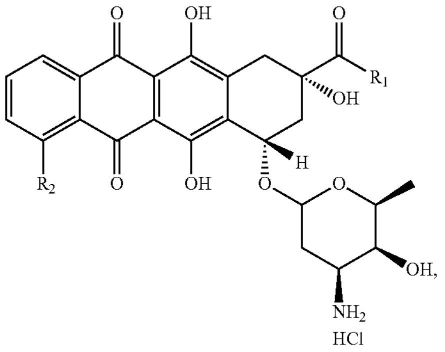

Formula (2)

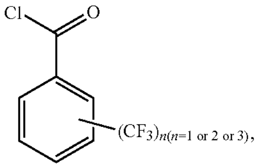

Formula (3)

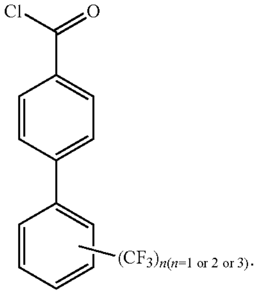

In one embodiment, the steps of the method include: dissolving the compound represented by Formula (1) in an organic solvent such as acetonitrile, adding an acid-binding agent such as triethylamine, and dropwise adding the compound represented by Formula (2) or the compound represented by Formula (3) at low temperature to acylate the amino group to yield the desired fluorobenzoyl anthracycline derivative.

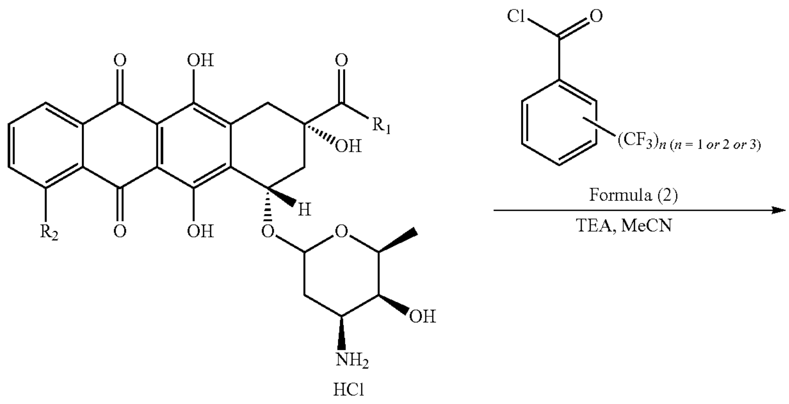

Formula (1)

-continued

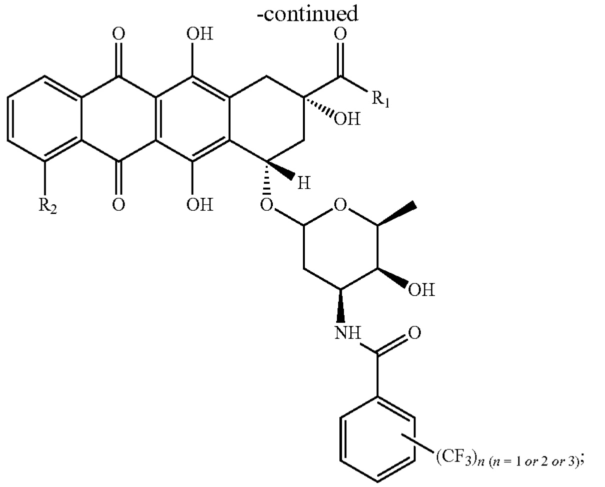

;

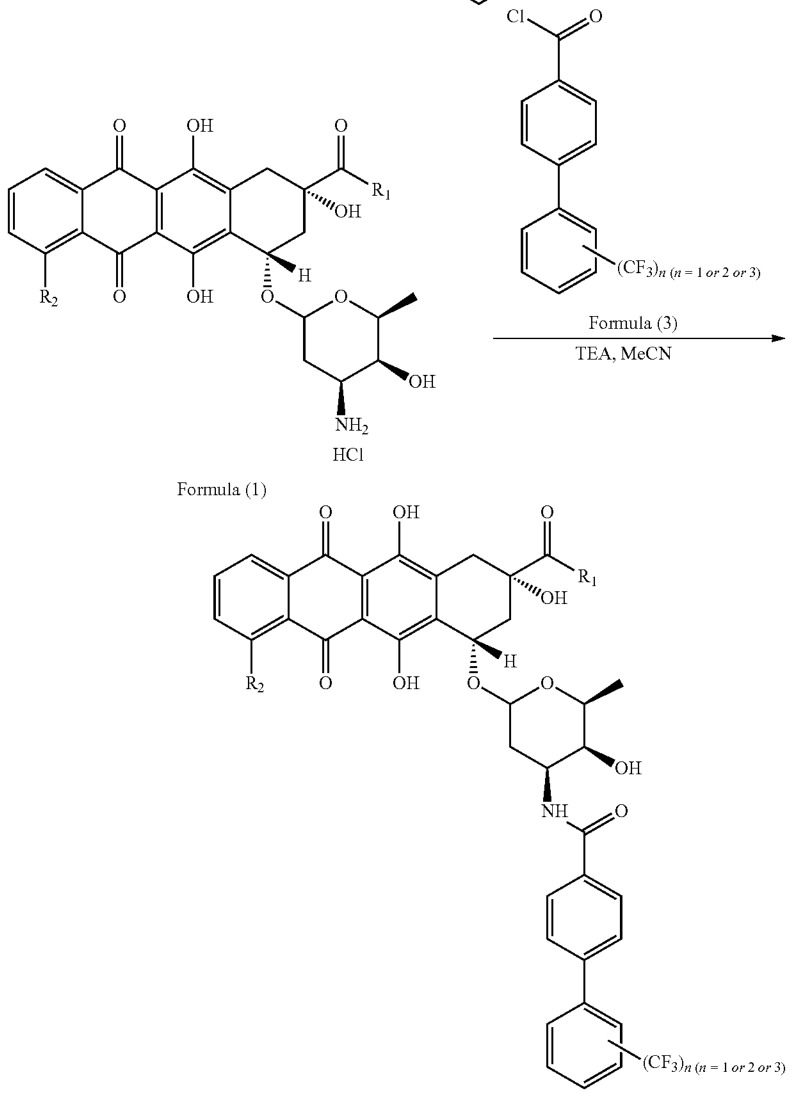

Formula (1)

In one embodiment, the synthesis route of the trifluoromethylphenyl-substituted benzoyl chloride represented by Formula (3) includes using tetrakis(triphenylphosphine) palladium as a catalyst, sodium carbonate as a base, and a mixture of 1,4-dioxane and water as a reaction solvent, reacting 4-iodobenzoic acid with mono-, di- or tri-trifluoromethylphenylboronic acid (i.e., trifluoromethyl mono-, di- or tri-substituted phenylboronic acid) via a SUZUKI coupling reaction to generate 4-mono-, di- or tri-trifluoromethylphenylbenzoic acid (i.e., 4-(trifluoromethylphenyl)benzoic acid), and reacting the generated product with thionyl chloride to obtain 4-mono-, di- or tri-trifluoromethylphenylbenzoyl chloride (i.e., 4-(trifluoromethylphenyl)benzoyl chloride).

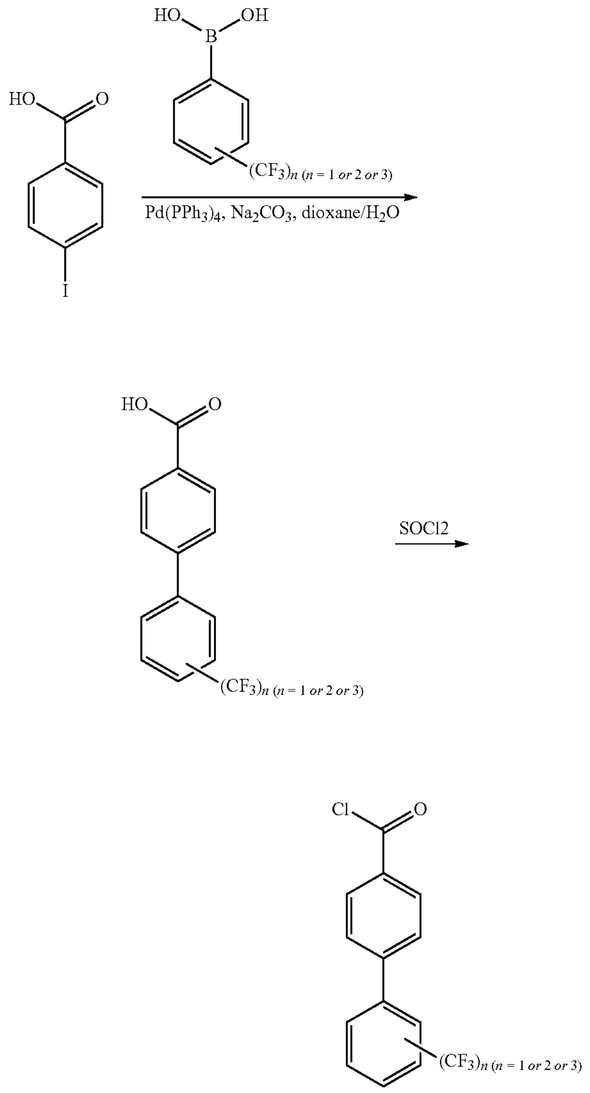

In a third aspect, the invention relates to applications of the fluorobenzoyl anthracycline derivatives described above as an ablation medium for heterogeneous myocardial ablation.

In one embodiment, the heterogeneous myocardium mainly includes two categories:

1) Heterogeneous myocardium with abnormal myocardial proliferation, such as hypertrophic cardiomyopathy, severe left ventricular outflow tract obstruction in hypertrophic cardiomyopathy, requiring ventricular septal volume reduction therapy.
2) Heterogeneous myocardium with abnormal cardiac electrical activity, which can cause arrhythmias, and severe malignant arrhythmias, which can be life-threatening.

When used as an ablation medium, the fluorobenzoyl anthracycline derivatives induce cell necrosis and/or functional loss in the heterogeneous myocardium, thereby relieving left ventricular outflow tract obstruction or eliminating malignant arrhythmias.

The fluorobenzoyl anthracycline derivatives can be primarily used for chemical ablation treatment of hypertrophic cardiomyopathy.

Advantages of the invention: The invention involves a class of the fluorobenzoyl anthracycline derivatives obtained by derivatizing the amino groups of anthracycline derivatives with fluorobenzoyl groups. These compounds establish specific biochemical target effects, including a highly efficient "first-pass effect" and "self-localization endothelial injury". One of the foundations of this invention is the highly efficient "first-pass effect". The fluorobenzoyl-containing anthracycline derivatives serve as an ablation medium delivered via catheter intervention. When the ablation medium is distributed through the bloodstream to the local arterial endothelium of the heart, its efficient "first-pass effect" ensures targeted distribution and optimal utilization of the medium. In synergy with the ablation medium, the endothelium of intramural penetrating resistance arteries interacts, remarkably achieving "self-localization endothelial injury".

This injury only induces microarterial-level blood flow attenuation, leading to precisely targeted myocardial ischemia and necrosis under dual-targeting integration.

Thus, the fluorobenzoyl-containing anthracycline derivatives provided by this invention can be applied via interventional procedures for the treatment of heart diseases. Through the aforementioned dual-targeting effects, the regional endothelium of intramural penetrating resistance arteries undergoes conditional injury, causing microarterial blood flow attenuation in the targeted area. Consequently, the ischemic heterogeneous myocardium sustains injury or necrosis. Two technical pathways generate biological targeting-induced endothelial injury responses, while dual spatial interactive guidance technology enhances the benefit/risk ratio of ischemic myocardial ablation. For example, a new precise, self-regulated chemical ablation procedure can be developed for hypertrophic cardiomyopathy-related left ventricular outflow tract obstruction. Due to the well-defined therapeutic effects of the ablation medium, which features regional targeting and precise tissue injury, the success rate is improved, significantly reducing the risks and complications associated with interventional ablation procedures.

The synthesis process is straightforward, and raw materials are readily available, facilitating industrial-scale production.

DETAILED DESCRIPTION OF THE INVENTION

Figure 1:
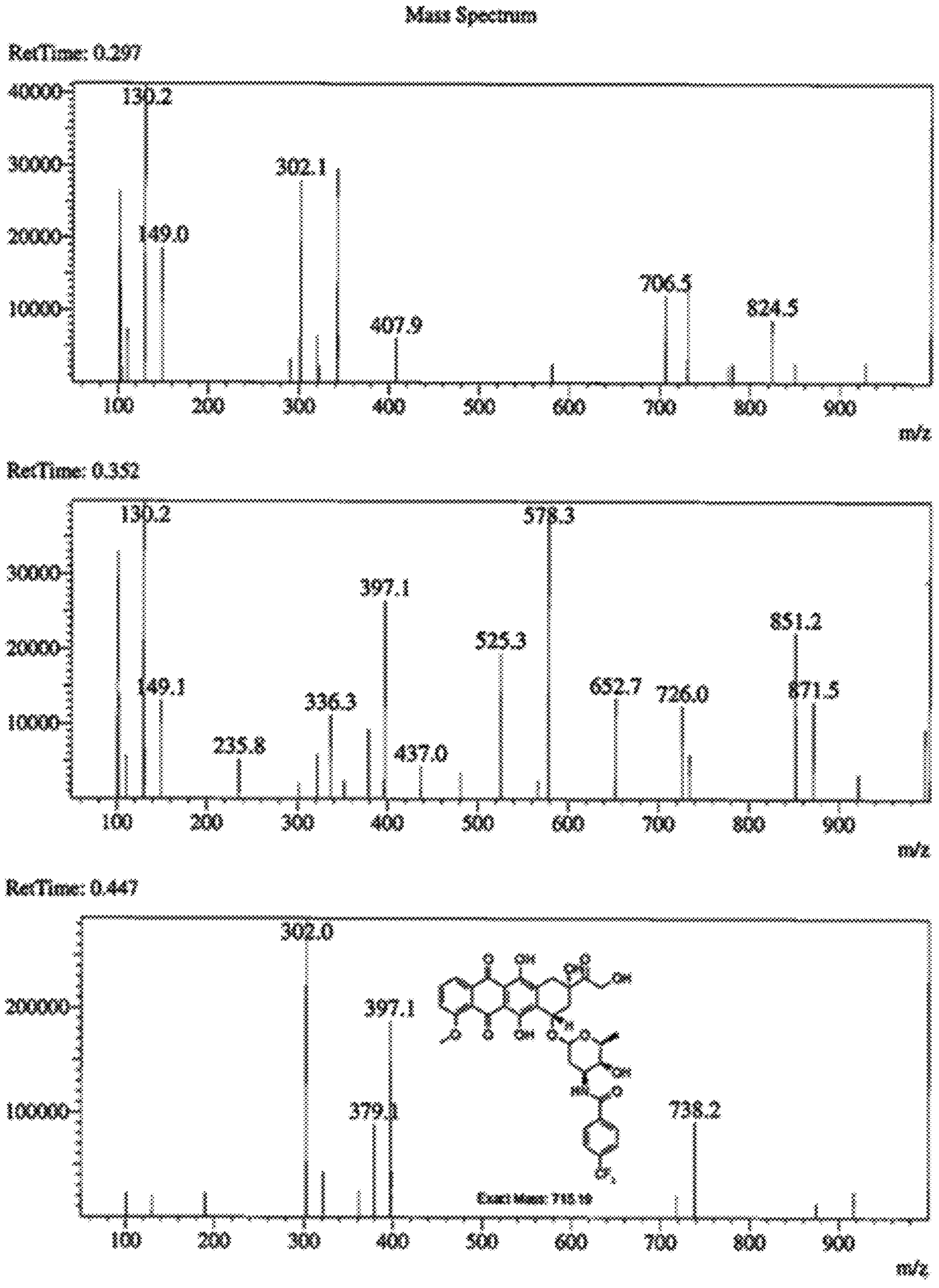
FIGS. 1-4 shows respectively mass spectrometry (MS), liquid chromatography-mass spectrometry (LC-MS), proton nuclear magnetic resonance (HNMR), and fluorine nuclear magnetic resonance (FNMR) of Compound 1, according to embodiments of the invention.
Figure 2:
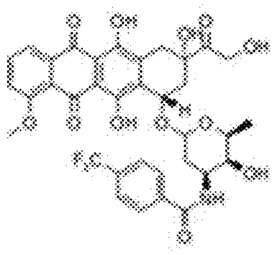
Figure 2:
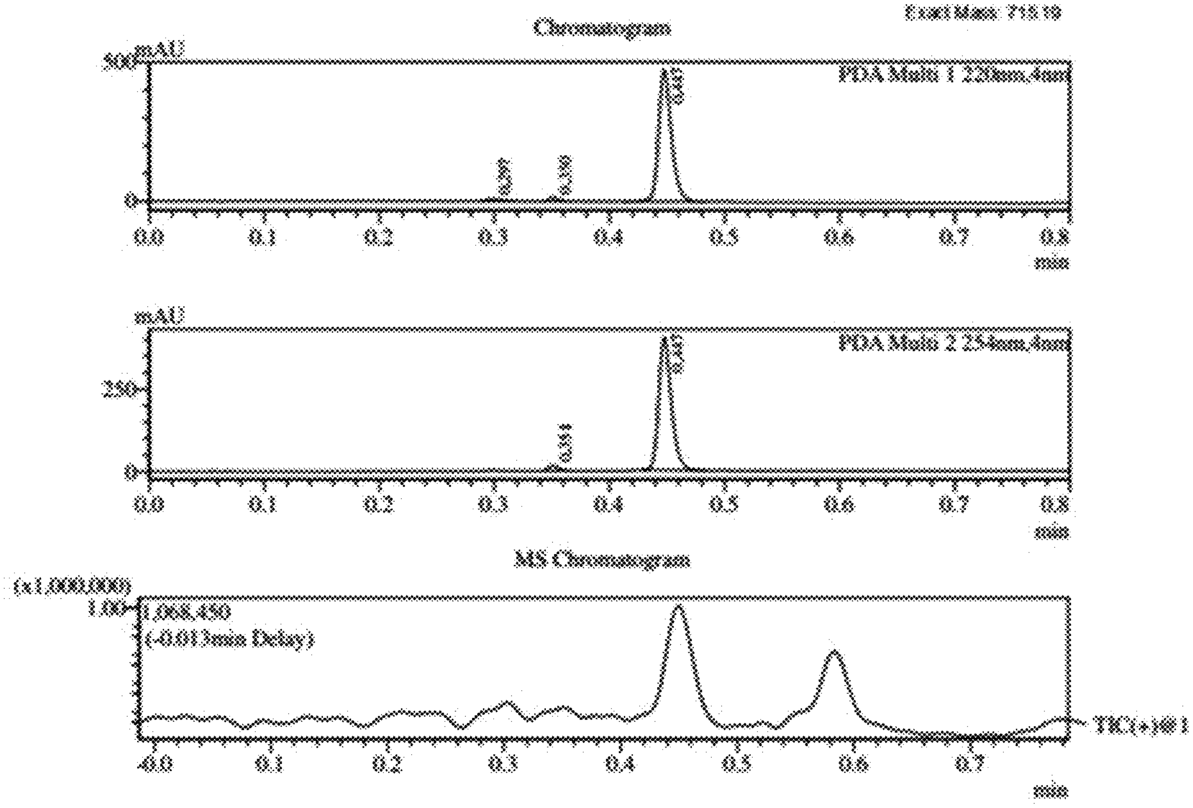
Figure 3:
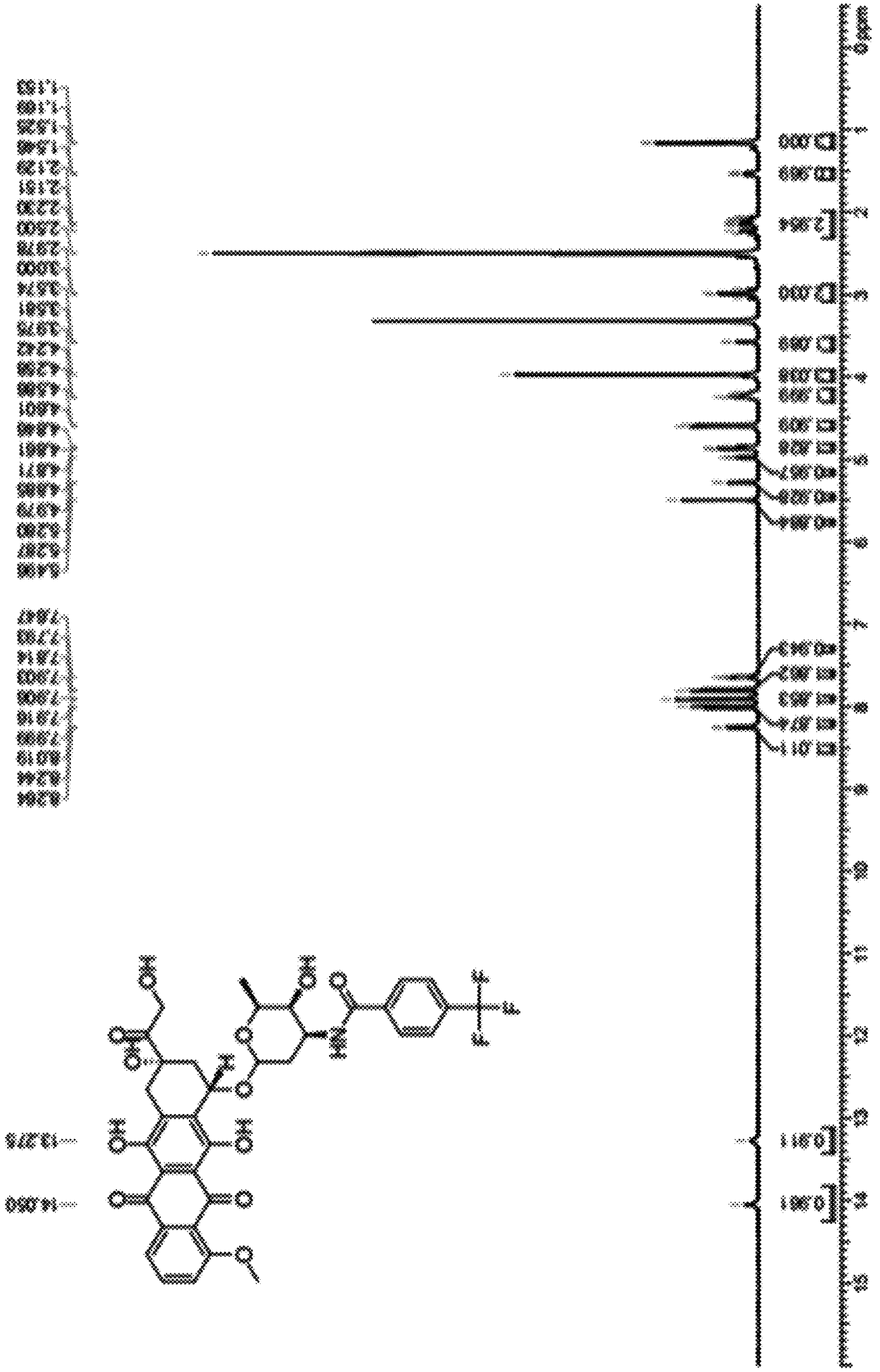
Figure 4:
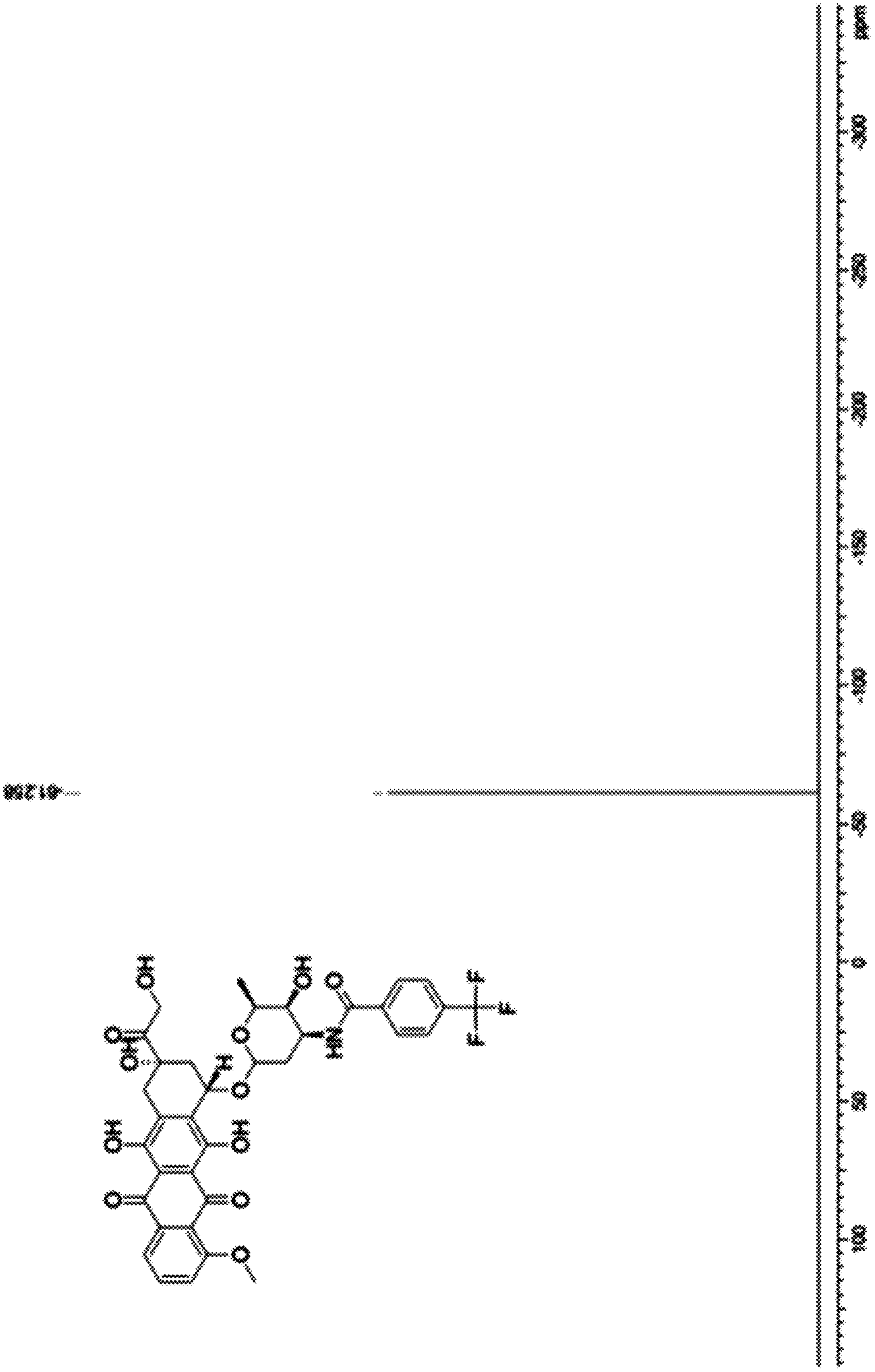
Figure 5:
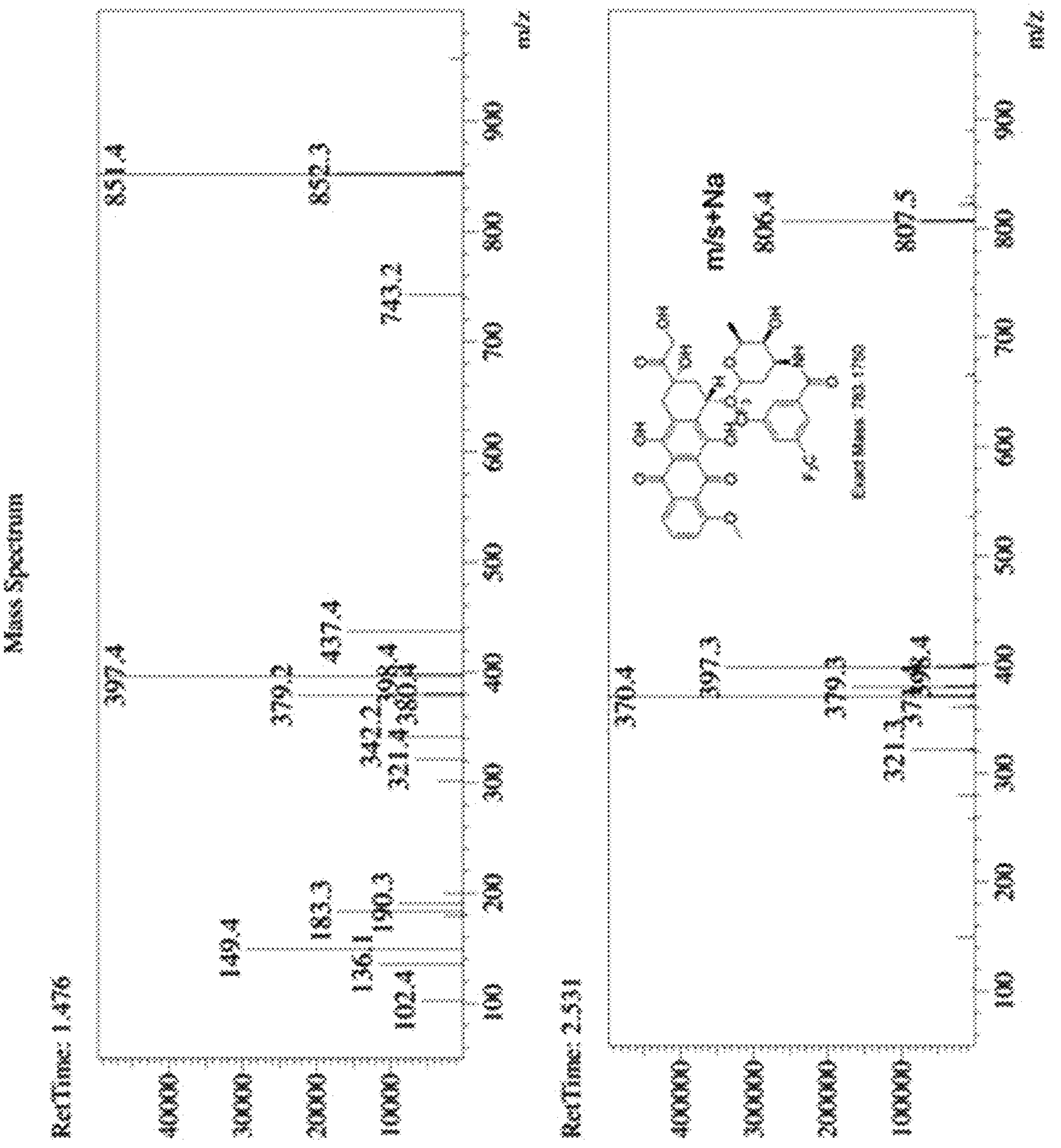
FIGS. 5-8 shows respectively MS, LC-MS, HNMR, and FNMR of Compound 2, according to embodiments of the invention.
Figure 6:
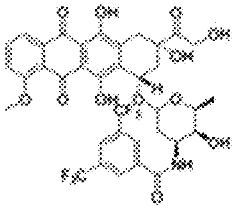
Figure 6:
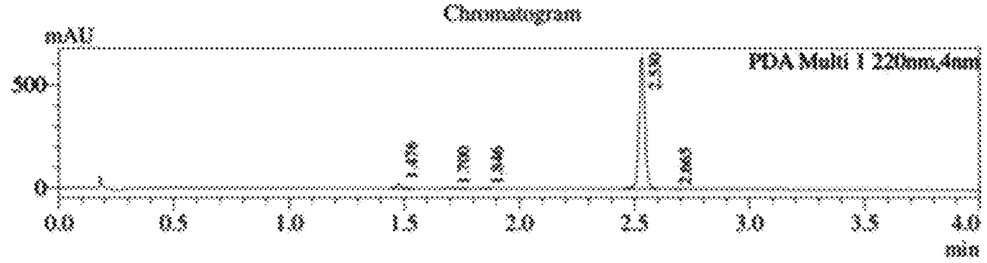
Figure 6:
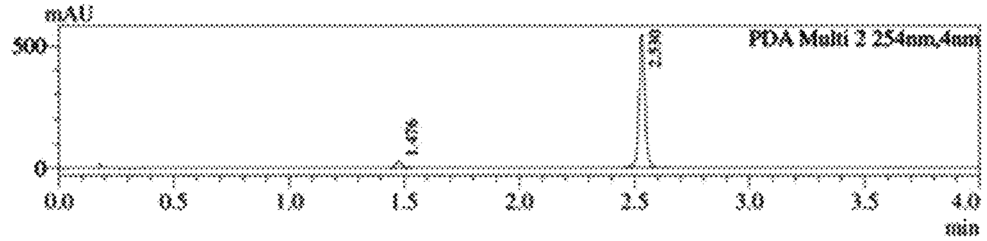
Figure 6:
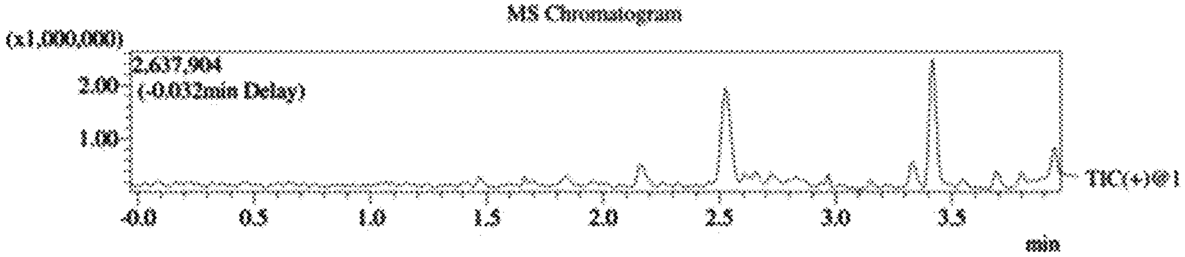
Figure 7:
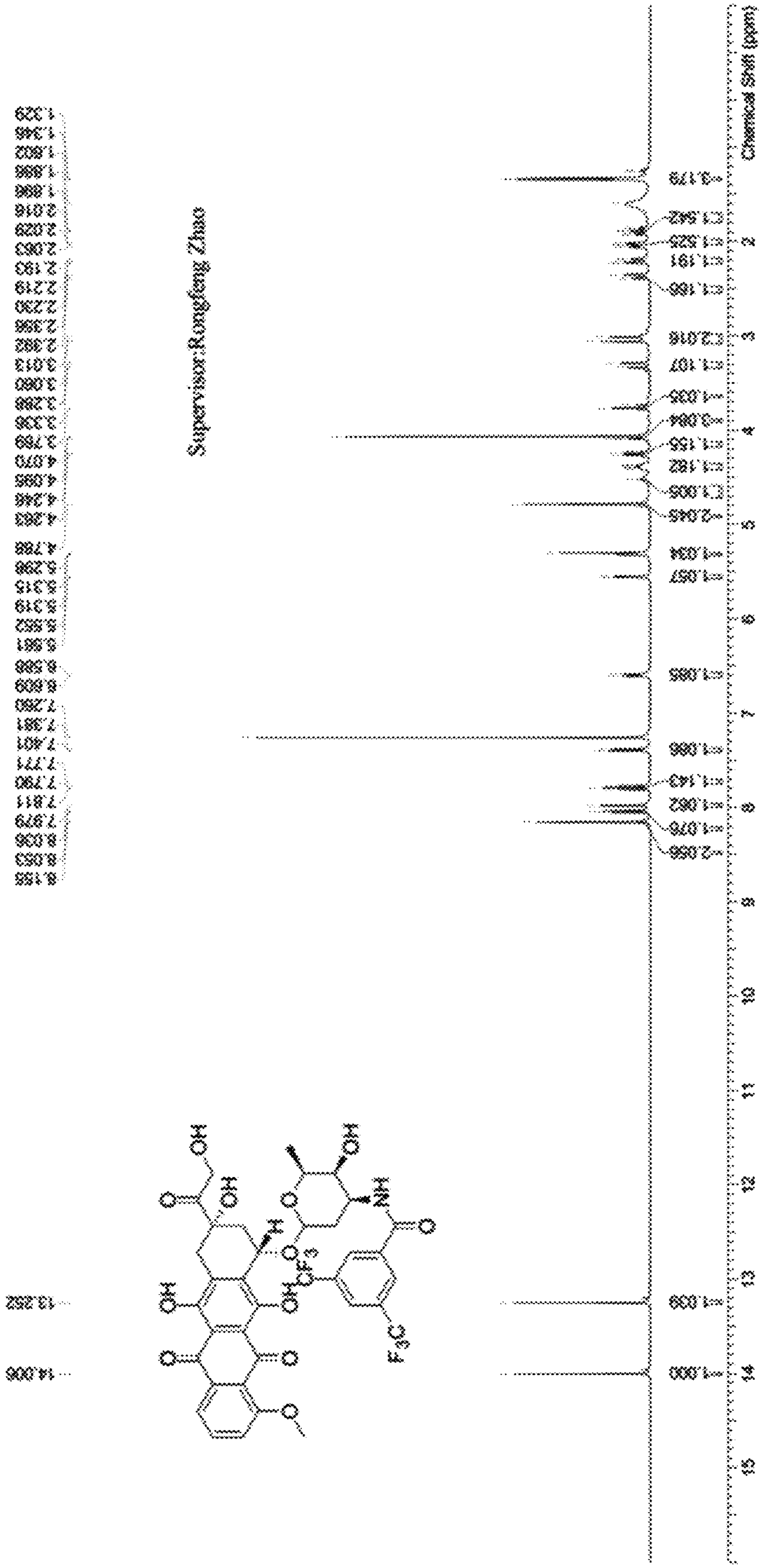
Figure 8:
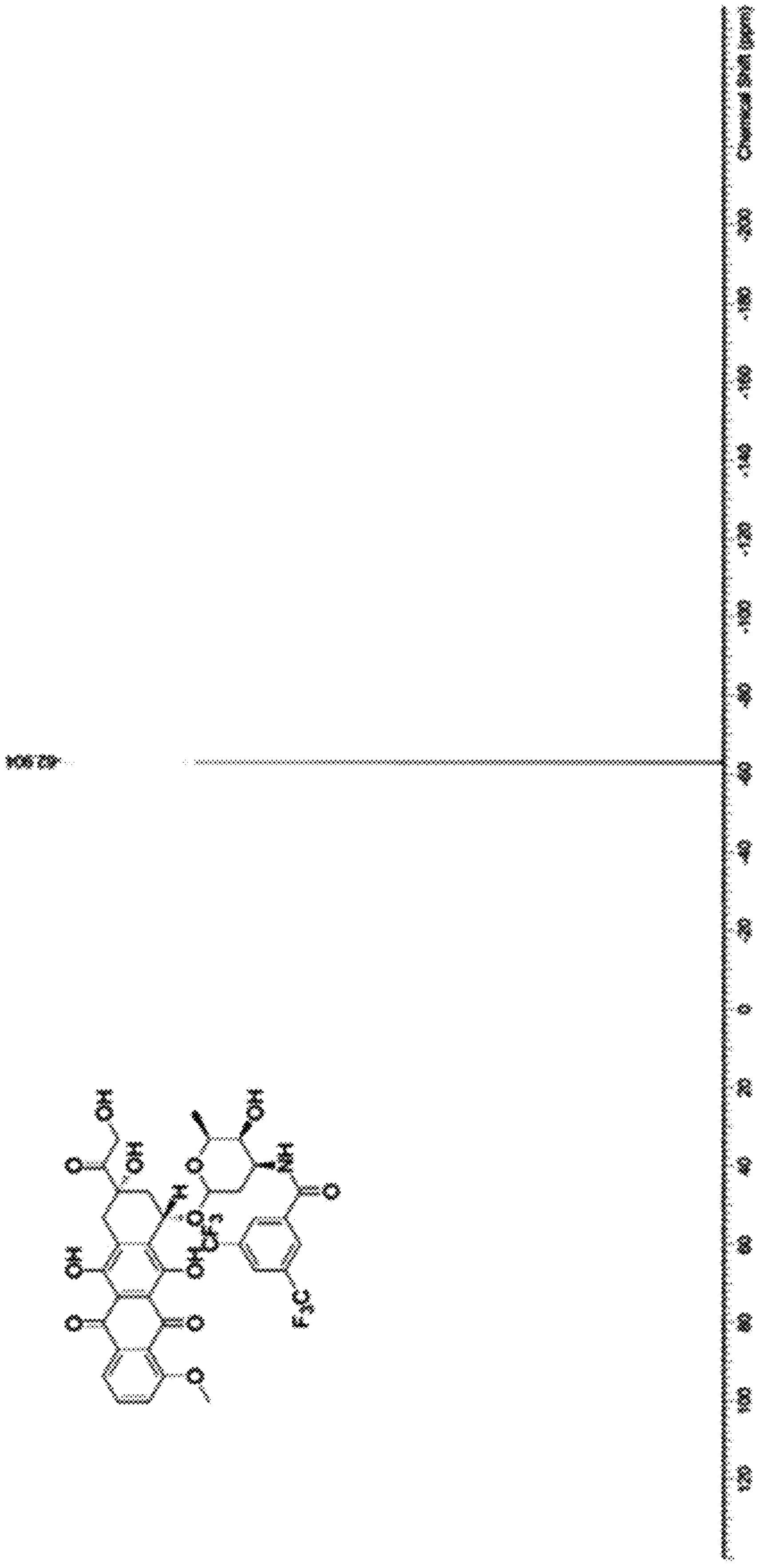
Figure 9:
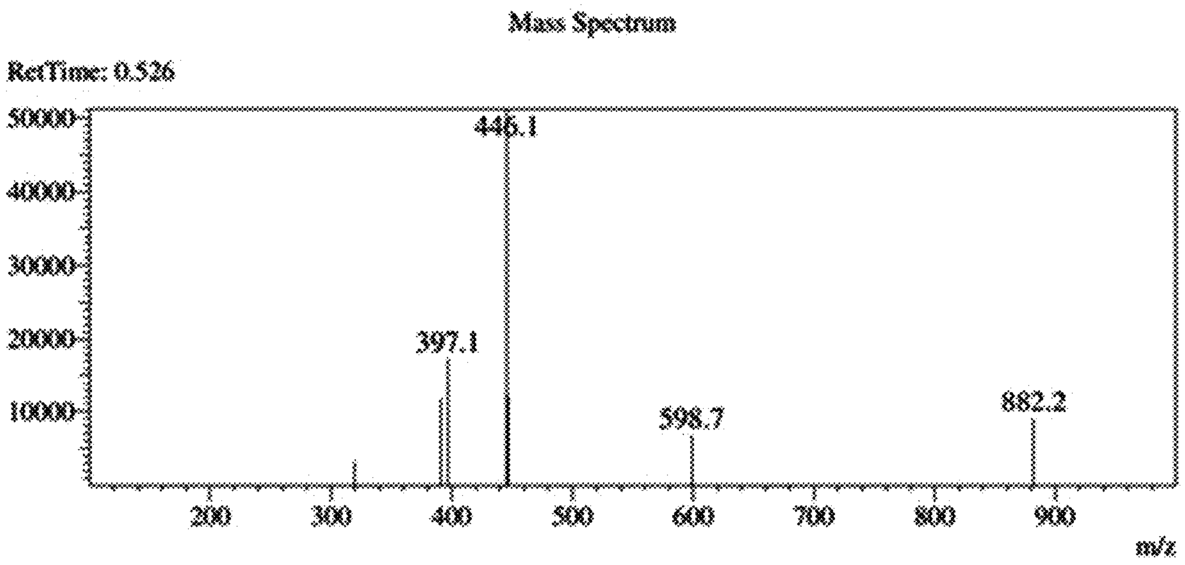
FIGS. 9-12 shows respectively MS, LC-MS, HNMR, and FNMR of Compound 3, according to embodiments of the invention.
Figure 9:
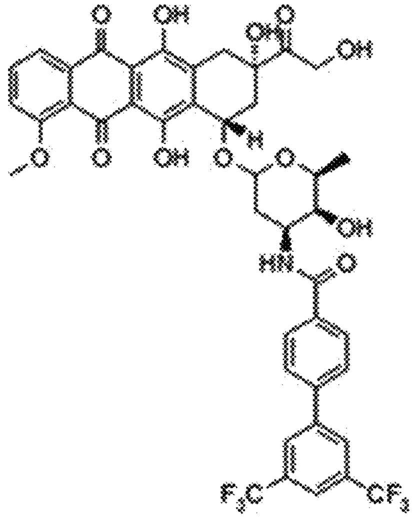
Figure 10:
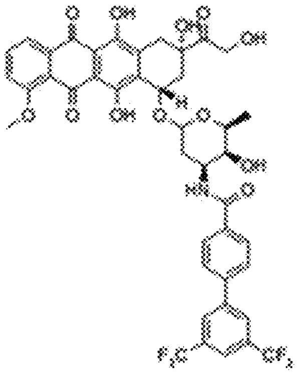
Figure 10:
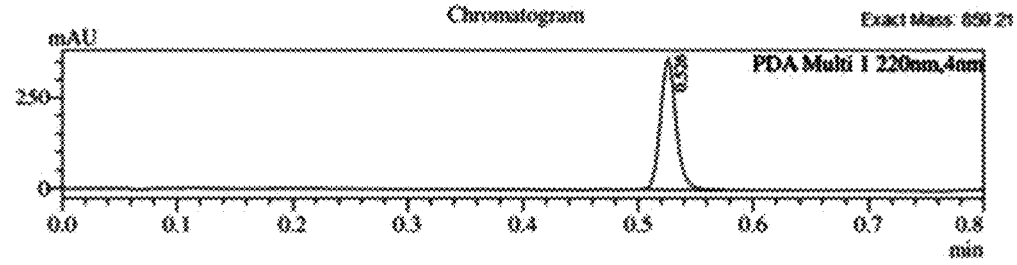
Figure 10:
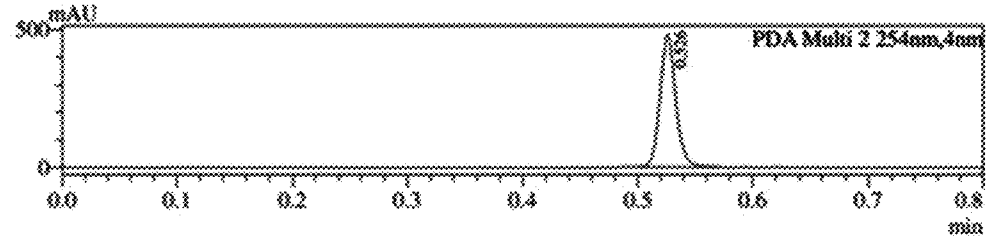
Figure 10:
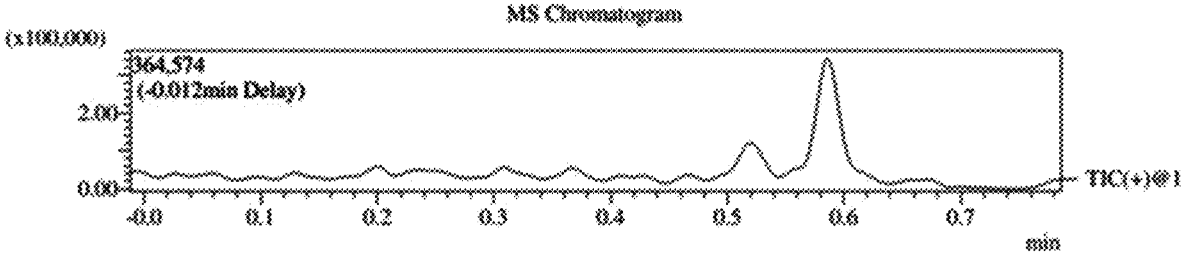
Figure 11:
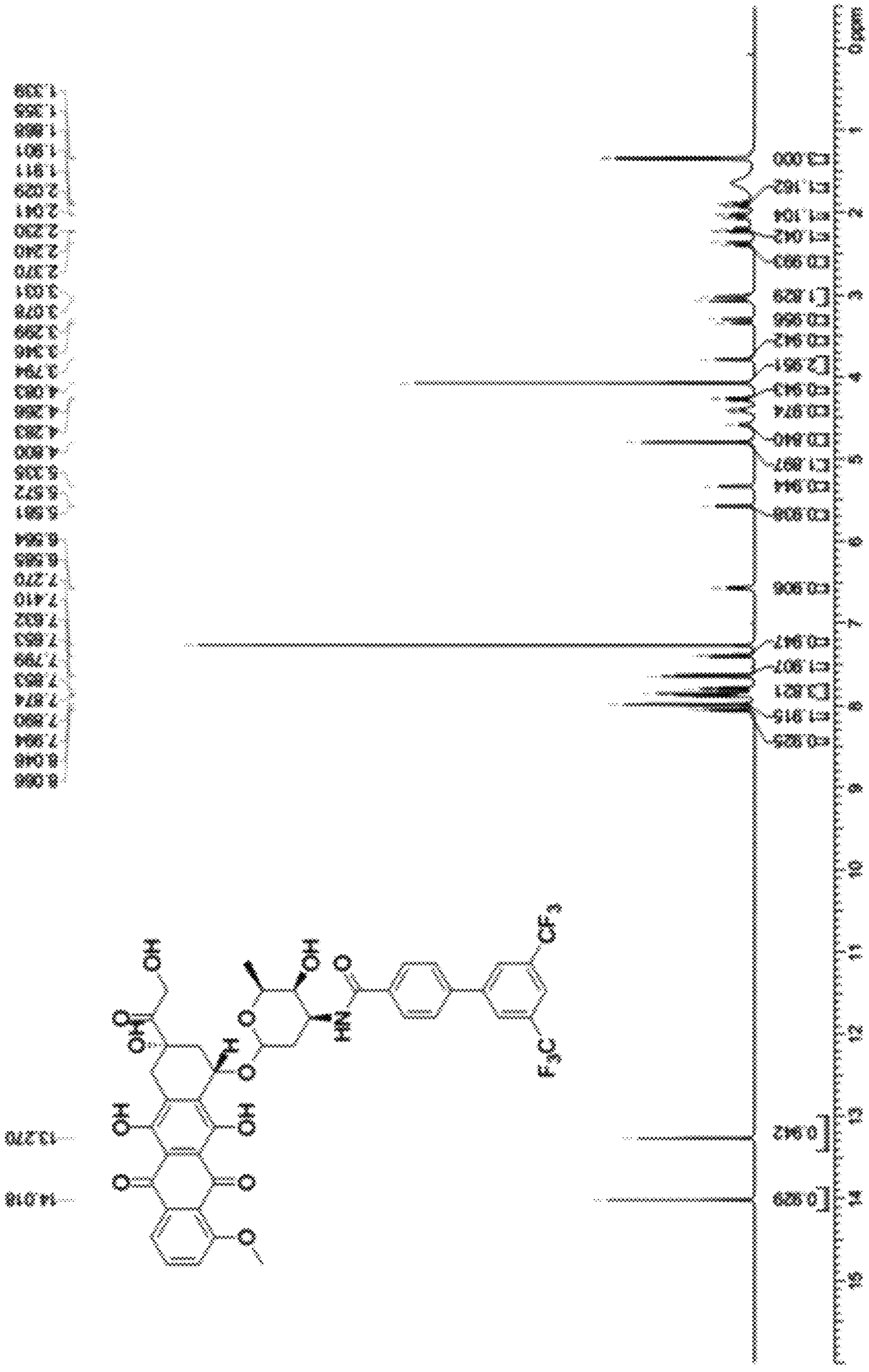
Figure 12:
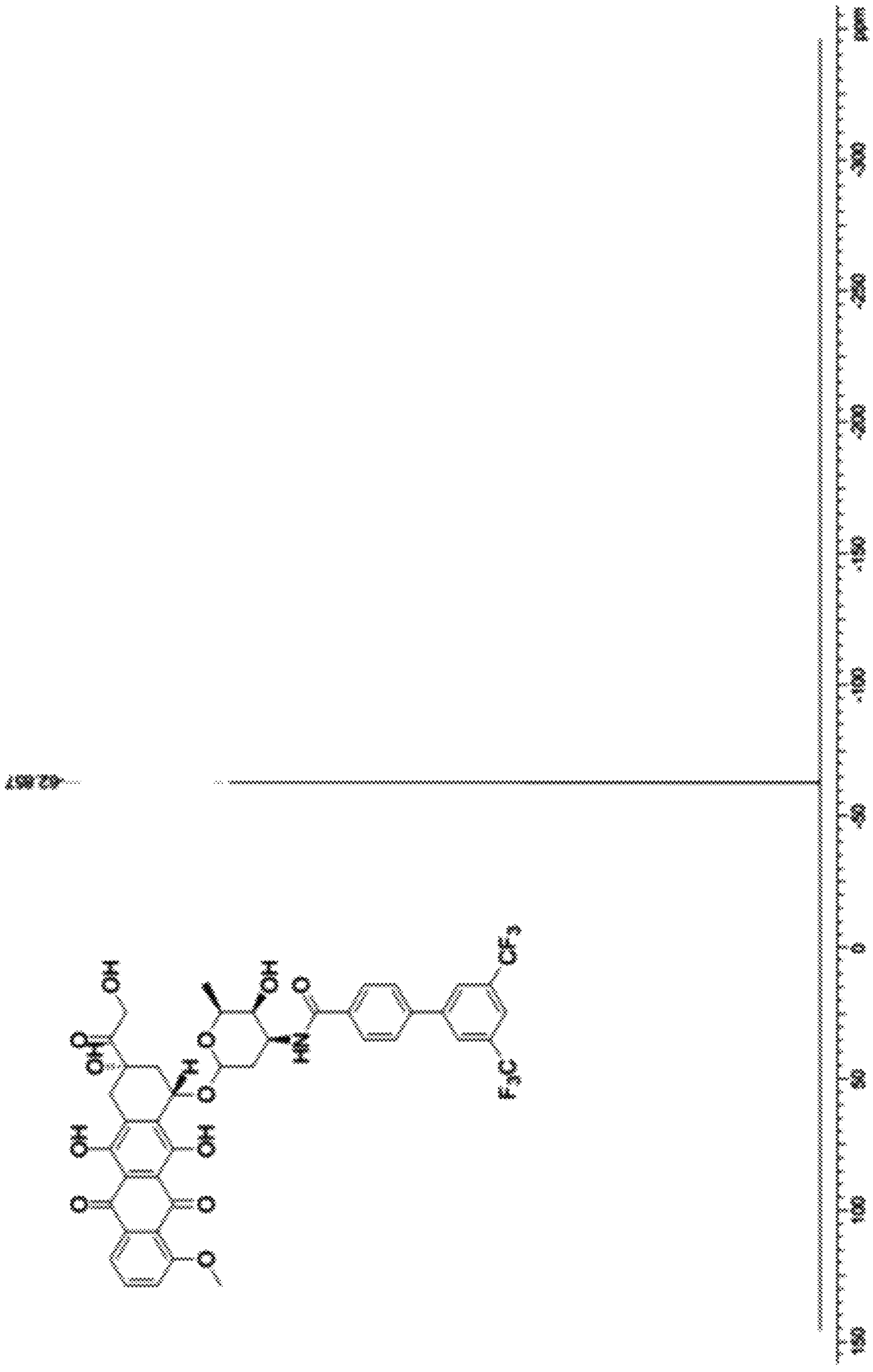

To further clarify the objectives, technical solutions, and advantages of this invention, the following detailed description is provided with reference to figures and examples. The examples are illustrative and do not limit the invention.

The invention involves the derivatization of fluorobenzoyl groups on the amino group of anthracycline derivatives. The resulting compounds serve as ablation media with characteristics of targeted localization and controllable damage, demonstrating high effectiveness and safety for heterogeneous myocardial chemical ablation. The novel ablation medium can be utilized to improve the ASA procedure, inducing ischemic necrosis in the target myocardium with reduced procedural and post-procedural complications. The implementation of three specific derivatives, namely 4-trifluoromethylbenzoyl, 3,5-trifluoromethylbenzoyl, and 2,4,6-trifluoromethylbenzoyl derivatives, is detailed below.

The terms "fluorinated benzoyl anthracycline derivatives" and "fluorobenzoyl anthracycline derivatives", used in the disclosure, are exchangeable and refer to a class of anthracene ring structure derivatives containing fluorinated benzoyl groups.

Embodiment 1: Synthesis of Fluorobenzoyl Anthracycline Derivatives

Synthesis of Compound 1:

Compound A (500 mg, 919 μmol, 1.00 eq) was dissolved in dichloromethane (20 mL), with triethylamine (279 mg, 2.76 mmol, 384 μL, 3.00 eq) and Compound a (287 mg, 1.38 mmol, 205 μL, 1.50 eq) added.

The mixture was stirred at 25° C. for 2 hours. LC-MS (EC22858-1-P1A) confirmed the consumption of Compound A and the formation of the desired product.

The reaction mixture was concentrated under reduced pressure to obtain a residue. The product was purified by pre-HPLC column: CD01-Phenomenex luna C18 150*25*10 μm, mobile phase: water (FA)-ACN, gradient: 36%-66% B, time: 8 min, and analyzed by HPLC (EC22858-1-P1C6), LCMS (EC22858-1-P1E2), HNMR (EC22858-1-P1A1), and FNMR (EC22858-1-P1F1), yielding Compound 1 as a red solid (168 mg, 159 μmol, 17.32% yield, 95.0% purity).

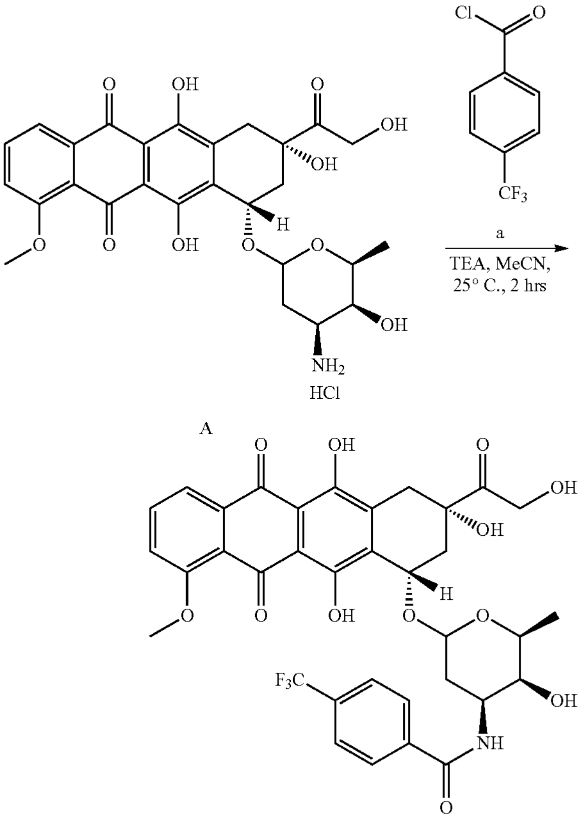

FIGS. 1-4 shows respectively MS, LC-MS, HNMR, and FNMR of Compound 1, wherein the specific data are as follows:

LC-MS: RT=0.447 min, $[M+Na]^+$=738.2; HNMR: δ 14.06 (br s, 1H), 13.51-12.85 (m, 1H), 8.26 (d, J=7.6 Hz, 1H), 8.02 (d, J=8.1 Hz, 2H), 7.95-7.88 (m, 2H), 7.81 (d, J=8.4 Hz, 2H), 7.70-7.62 (m, 1H), 5.50 (s, 1H), 5.29 (br d, J=3.2 Hz, 1H), 5.04-4.95 (m, 1H), 4.94-4.78 (m, 2H), 4.60 (d, J=6.0 Hz, 2H), 4.33-4.16 (m, 2H), 3.98 (s, 3H), 3.59 (br d, J=2.8 Hz, 1H), 3.10-2.88 (m, 2H), 2.33-2.03 (m, 3H), 1.54 (br dd, J=4.1, 12.0 Hz, 1H), 1.17 (d, J=6.4 Hz, 3H).

Synthesis of Compound 2:

Triethylamine (366 mg, 3.62 mmol, 504 μL, 2.10 eq) and compound b (525 mg, 1.90 mmol, 344 μL, 1.1 eq) were added to a solution of compound A (1.00 g, 1.72 mmol, 1.00 eq) in acetonitrile (300 mL) to form a mixture thereof.

The mixture was stirred at 25° C. for 2 hours under $N_2$ environment. TLC monitoring (platel: dichloromethane: methanol=2:1) showed residual compound A (Rf=0.00), and 3 major new spots were detected (Rf=0.50, Rf=0.59, Rf=0.71), and the product Rf was 0.50. LC-MS (EC10154-49-P1C) showed that compound A remained 36.42%. LC-MS showed a new peak, and the target compound was detected to account for 53.74%.

The reaction mixture was quenched with 20 mL of water at 25° C. and extracted with 150 mL of dichloromethane (50 mL×3). The organic layers were combined, dried with anhydrous magnesium sulfate, filtered under reduced pressure, and the filtrate was concentrated to obtain a crude product. It was purified by preparative high-performance liquid chromatography (trifluoroacetic acid conditions).

The mixed solution was diluted with water (1000 ml) and extracted with dichloromethane 2000 ml (1000 ml×2). The organic layers were combined, washed with 1000 ml of water (500 ml×2), washed with $NaHCO_3$1000 ml (5%, 500 ml×2), washed with 1000 ml of water (500 ml×2), dried with $Na_2SO_4$, filtered, and concentrated under reduced pressure to obtain the product of Compound 2.

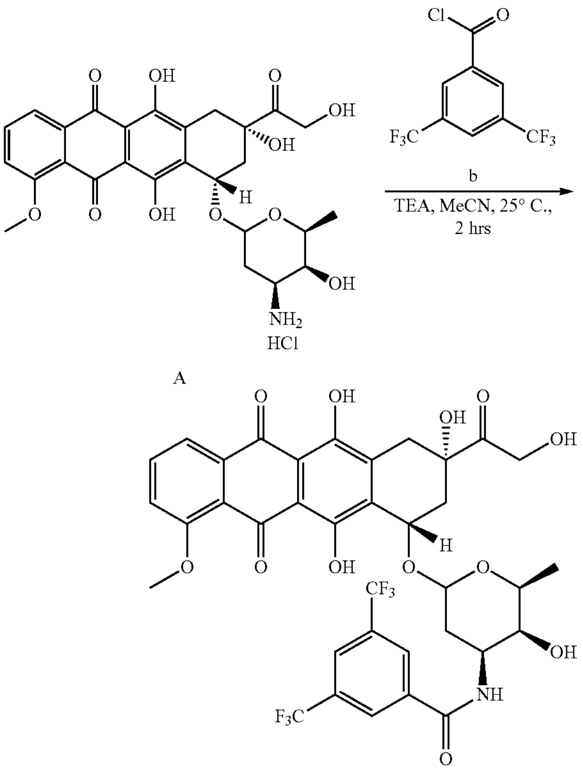

A

FIGS. 5-8 shows respectively MS, LC-MS, HNMR, and FNMR of Compound 2, wherein HNMR data are as follows: δ=1.34 (d, J=6.8 Hz, 3H) 1.89 (td, J=13.2, 4.0 Hz, 1H) 2.00-2.07 (m, 2H) 2.18-2.24 (m, 1H) 2.34-2.41 (m, 1H) 2.99-3.08 (m, 2H) 3.31 (dd, J=18.8, 1.2 Hz, 1H) 3.77 (br s, 1H) 4.05-4.08 (m, 3H) 4.25 (q, J=6.4 Hz, 14.35-4.43 (m, 1H) 4.47-4.57 (m, 1H) 4.79 (s, 2H) 5.28-5.31 (m, 1H) 5.56 (d, J=3.6 Hz, 1H) 6.60 (br d, J=8.4 Hz, 1H) 7.39 (d, J=8.00 Hz, 1H) 7.77-7.82 (m, 1H) 7.96-7.99 (m, 1H) 8.04 (dd, J=7.6, 0.8 Hz, 1H) 8.12-8.18 (m, 2H) 13.25 (s, 1H) 14.01 (s, 1H).

LCMS (EC10154-49-P1F6_LCMS_WH, $R_t$=2.530 min) confirms the structure.

Synthesis of Compound 3:

Compound c (21.0 g, 84.6 mmol, 1.00 eq) and compound d (22.9 g, 88.9 mmol, 1.05 eq) were dissolved in 1,2-dioxane (200 mL) and water (50 mL), and $Na_2CO_3$ (17.9 g, 169 mmol, 2.00 eq) and $Pd(PPh_3)_4$ (4.89 g, 4.23 mmol, 0.050 eq) were added, to form a mixture thereof.

The mixture was stirred at 25° C. for 12 hours. LC-MS (EC16604-133-P1A) showed that reactant d was completely consumed and the required mass was detected. The reaction mixture was filtered and concentrated under reduced pressure to obtain a residue. The reaction solution was diluted with 500 mL of water and ethyl acetate (500 mL) was extracted three times. The combined organic layers were dried over $Na_2SO_4$ and concentrated under reduced pressure to remove the solvent. Purification was performed by flash silica gel chromatography (ISCO®); 35 g SepaFlash® silica gel flash column, eluent was 0-30% ethyl acetate/petroleum ether gradient, TLC: petroleum ether:ethyl acetate=3/1). Compound e (11.0 g, 59.8 mmol, yield 40.6%) was a white solid.

Compound e (2.00 g, 5.98 mmol, 1.00 eq) was added to toluene (20 mL). SOCl2 (854 mg, 7.18 mmol, 521 μL, 1.20 eq) 20 mL was added. Stir at 80° C. for 3 hours. TLC (polarity: petroleum ether:ethyl acetate=5/1) showed that reactant 1 was completely consumed and a product spot was formed (RF=0.65). The reaction mixture was concentrated under reduced pressure to obtain a residue. The crude product was directly used in the next step to obtain compound f (2.00 g, crude product) as a white solid.

Compound A (1.50 g, 2.76 mmol, 1.00 eq) was dissolved in dichloromethane (38 mL), TEA (837 mg, 8.28 mmol, 1.15 mL, 3.00 eq) and compound f (973 mg, 2.76 mmol, 1.00 eq) were added, and stirred at 25° C. for 2 hours. LC-MS (EC22858-10-P1A2) showed that reactant 1 was completely consumed and the desired mass was detected (retention time=0.526 min). The reaction mixture was concentrated under reduced pressure to obtain a residue. Purification was performed by column chromatography ($SiO_2$, eluent: dichloromethane/methanol=100/1~20/1, RF-0.7). Purification was performed by pre-HPLC (column: CD05-Phenomenex luna C18 150*40*10 μm, mobile phase: [water (FA)-ACN], gradient: 51%~81% B, over 10 min). Compound 3 (239 mg, 278 μmol, yield 11.9%) was obtained. LC-MS (EC22858-13-P1C2), HNMR (EC22858-13-P1A) confirmed it to be a red solid.

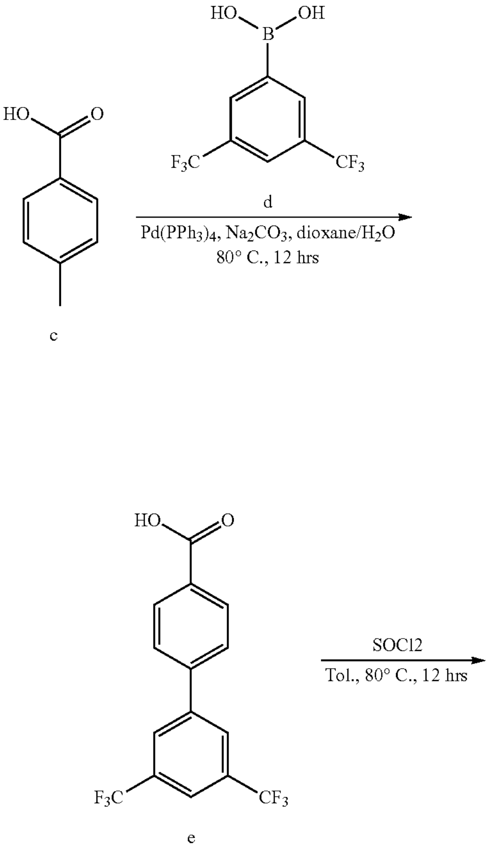

-continued

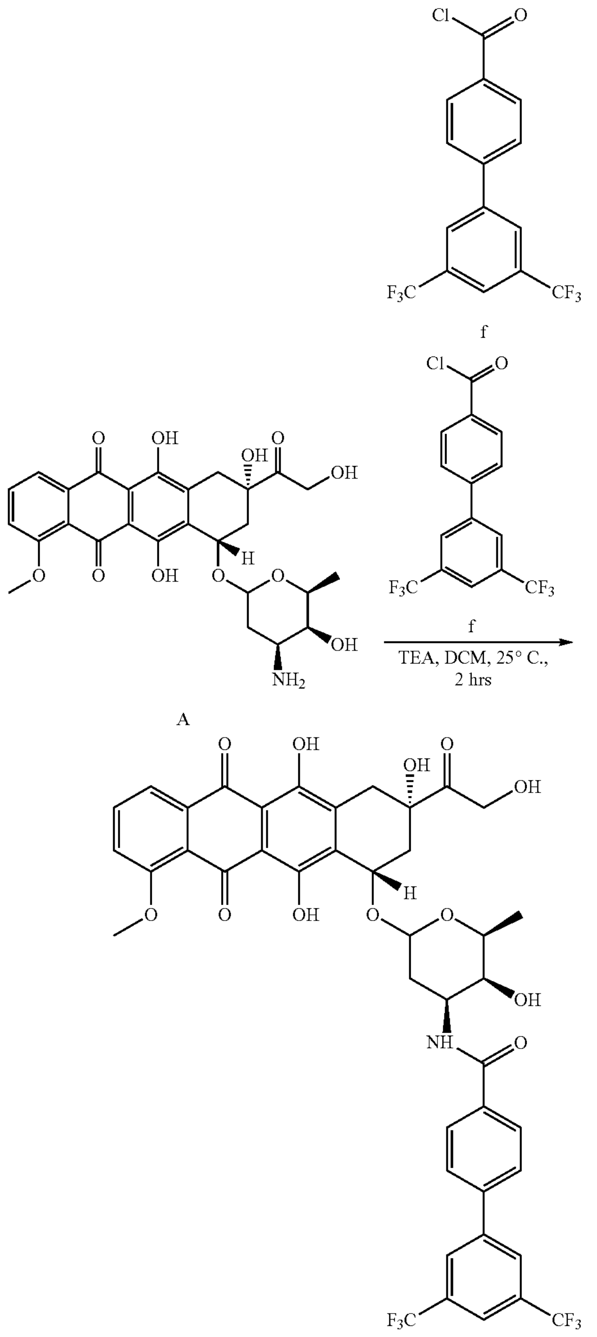

FIGS. 9-12 shows respectively MS, LC-MS, HNMR, and FNMR of Compound 3, wherein the specific data are as follows:

LC-MS: RT=0.526 min, $[M+Na]^+$=882.2; HNMR: § 14.02 (s, 1H), 13.27 (s, 1H), 8.06 (d, J=8.0 Hz, 1H), 7.99 (s, 2H), 7.93-7.74 (m, 4H), 7.64 (d, J=8.4 Hz, 2H), 7.40 (d, J=8.2 Hz, 1H), 6.57 (br d, J=8.4 Hz, 1H), 5.58 (d, J=3.6 Hz, 1H), 5.33 (br s, 1H), 4.80 (s, 2H), 4.59 (br s, 1H), 4.47-4.36 (m, 1H), 4.27 (q, J=6.4 Hz, 1H), 4.08 (s, 3H), 3.79 (br s, 1H), 3.32 (br d, J=18.8 Hz, 1H), 3.12-2.92 (m, 2H), 2.39 (br d, J=14.8 Hz, 1H), 2.22 (dd, J=3.9, 14.8 Hz, 1H), 2.05 (br dd, J=4.8, 13.2 Hz, 1H), 1.91 (dt, J=4.2, 13.2 Hz, 1H), 1.35 (d, J=6.4 Hz, 3H).

Embodiment 2: Interaction of Fluorobenzoyl Anthracycline Derivatives with Cardiac Endothelial Cells Objectives: To evaluate the interaction effect between the compound and the cardiac arterial endothelium, that is, the cardiac arterial endothelium is a special group of endothelial cells, which carries the pulsating cycle of heart contraction. This experiment simulates the cardiac pulsating cycle and constructs a cell culture model under the bionic pulsating cycle, in order to study the effect of the compound of the invention on endothelial cell viability and apoptosis under the bionic cycle.

Method: Coronary endothelial cells were passed to the third generation, and when the cell count reached the exponential growth phase, they were inoculated in a 96-well plate. The experimental groups are as follows: control group (without the compound of the invention), Compound 1, Compound 2, Compound 3, cardiac bionic pulsation+control group (without the compound of the invention), cardiac bionic pulsation+Compound 1, cardiac bionic pulsation+Compound 2, and cardiac bionic pulsation+Compound 3. Accurately weigh 5 mg of the compound, add an appropriate amount of DMSO to obtain a 10 μmol/L stock solution, and the final concentration of the added compound is 1 μmol/L.

Figure 13:
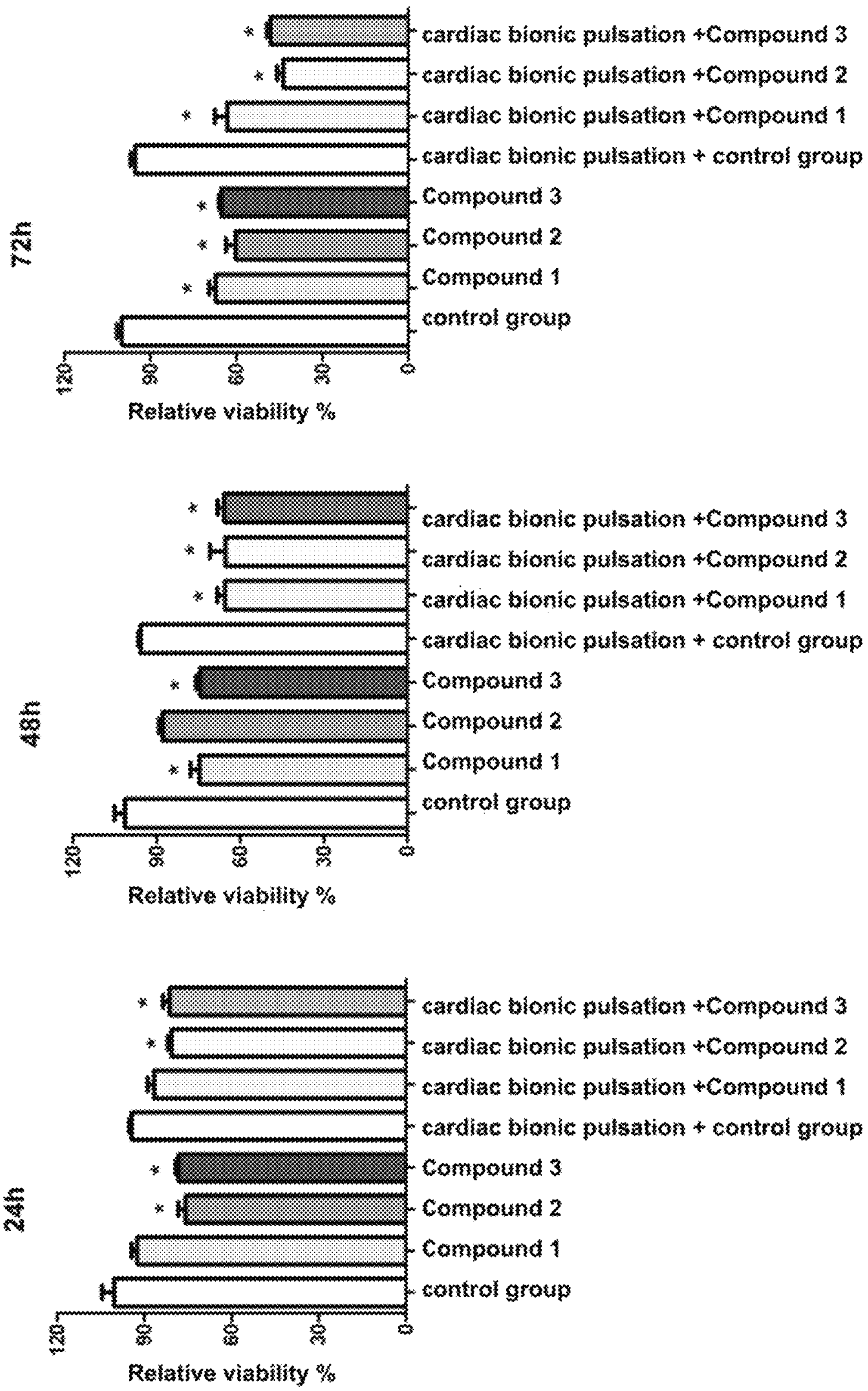
FIG. 13 shows effects of the fluorobenzoyl anthracycline derivatives on endothelial cell viability, according to embodiments of the invention.

Results: After 24 h, 48 h and 72 h of cell culture, the absorbance values of the above-mentioned groups of cells at 450 nm were detected by CCK-8 method to evaluate the effect of the interaction between cardiac arterial endothelium and compounds on cell viability. Relative viability (%)=(OD value of experimental group-background OD value)/(mean OD value of control group-background OD value)×100. The results of relative cell viability are shown in FIG. 13. The relative viability of the three groups of cells of Compound 1, Compound 2 and Compound 3 basically showed a downward trend with the extension of culture time. Under the interaction between cardiac arterial endothelium and compounds, the cell viability decreased significantly after 72 h of culture, and the cell viability of Compound 2 decreased the most.

Figure 14:
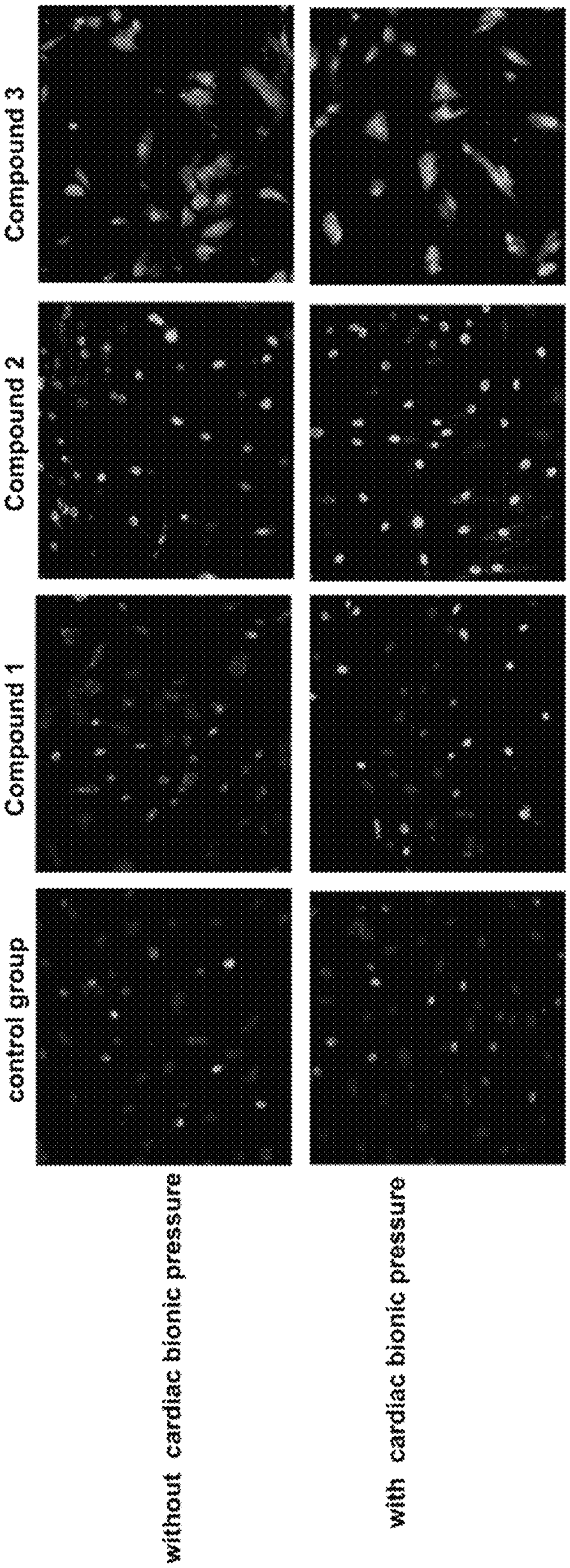
FIG. 14 shows endothelial cell apoptosis induced by the fluorobenzoyl anthracycline derivatives, according to embodiments of the invention.

Cardiac arterial endothelial cells were inoculated in 24-well plates and cultured for 24 hours. After the cells were placed on the plates, they were washed with PBS three times, each time for 3 minutes. Then, the cell slides were fixed with 4% paraformaldehyde for 30 minutes, and then the slides were washed with PBS three times, each time for 3 minutes. Subsequently, 0.5% Triton X-100 was used to permeabilize the membrane at room temperature for 20 minutes, and the slides were washed with PBS three times, each time for 3 minutes. Finally, the apoptosis of coronary endothelial cells was determined using the Tunnel kit. The results are shown in FIG. 14. Compound 1, Compound 2 and Compound 3 can all induce mild apoptosis of arterial endothelial cells. In comparison, when loaded with cardiac bionic pressure, the apoptosis of Compound 1, Compound 2 and Compound 3 increased significantly under the interaction of arterial endothelium and compounds. Relatively speaking, the apoptosis-promoting effect of Compound 2 and Compound 3 is better.

Embodiment 3: Effects of Compounds Targeting Damage to Endothelium of Cardiac Intramunal Penetrating Resistance Arteries Objectives: By intraperitoneal injection of compounds into mice, observe the compounds' targeted damage to the arterioles in the myocardial domain of the heart, and induce myocardial ischemia.

Figure 15:
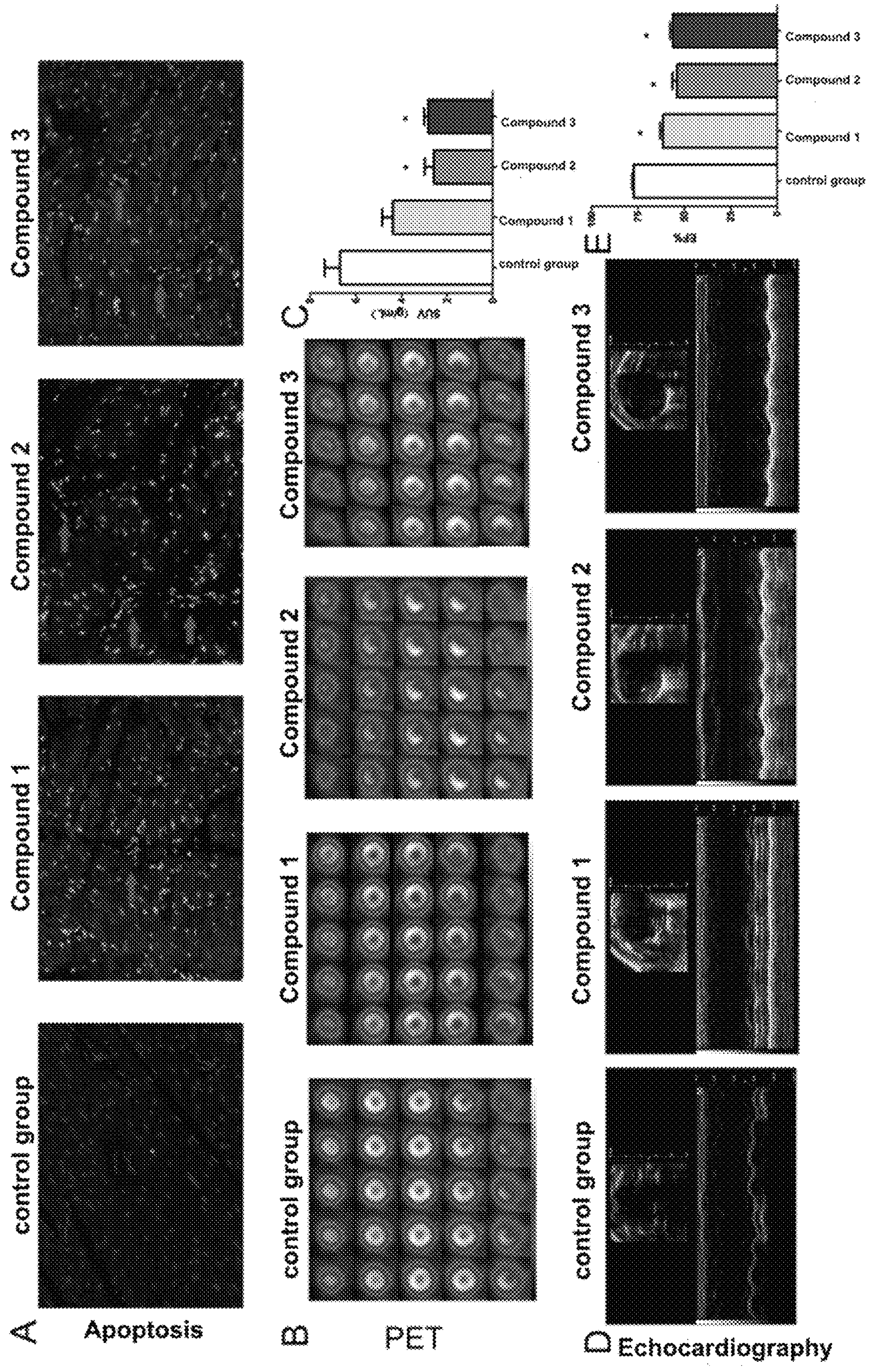
FIG. 15 shows a targeted damage to the percutaneous arterial endothelium by fluorobenzoyl anthracycline derivatives: cardiac arterial endothelial apoptosis (A), PET assessment of myocardial ischemia image (B), PET assessment of myocardial uptake SUV value (C), cardiac ultrasound image (D) and cardiac ejection fraction EF value (E), according to embodiments of the invention.

Methods and results: C57BL/6 mice, male mice, 8 weeks old, were intraperitoneally injected with a scalar compound of 40 mg/kg. After 7 days, the mouse's cardiac function was measured, PET-CT was used to evaluate myocardial ischemia, and immunofluorescence was used to detect arterial endothelial damage. The experiment found that apoptosis occurred in the endothelium of cardiac arterioles under the stimulation of compound 1, compound 2, and compound 3 (FIG. 15, A, indicated by the arrow); PET further indicated the attenuation of myocardial blood flow in mice (FIGS. 15, B and C); cardiac ultrasound EF values (FIGS. 15, D and E) showed that the cardiac function of mice was significantly downregulated under the action of Compound 1, Compound 2, and Compound 3, and relatively speaking, the damage effect of Compound 2 and Compound 3 was higher than that of Compound 1. The above results show that the compounds of the invention interact with the endothelial cells of cardiac arterioles, damage the intramunal penetrating resistance arteries, and produce conditional myocardial ischemia.

Embodiment 4: Directional Distribution and Biological Effects of Compounds in Porcine Coronary Arteries after Intervention Objectives: To understand the targeted distribution and biological effects of compounds in local cardiac tissues under the "first-pass effect" by measuring the concentration of compounds in the heart tissue of Bama miniature pigs.

Methods and results: 25-30 kg Bama miniature pigs were selected, and 0.1 ml/kg of Shutai was anesthetized by intramuscular injection, and 0.5 mg of atropine was injected intramuscularly after anesthesia. The experiment without the compound of the invention was designed as a control group.

First, the Bama miniature pigs were fixed in a supine position on the surgical wooden frame, and the chest and groin skin were prepared and disinfected. The twelve-lead electrocardiogram was measured before the operation. Then a 5F sheath was inserted into the femoral artery, and the catheter was sent to the left anterior descending branch of the coronary artery after coronary angiography. After measuring CFR, the compound of the invention was injected into the catheter at 4 mg/kg, and the injection was completed in 30 minutes. The twelve-lead electrocardiogram was measured 3 hours after the operation, and coronary angiography was performed in parallel. CFR was detected again after the operation to obtain the above data. After the pigs were euthanized, the heart was sampled, and the myocardial tissue of the left ventricular anterior descending branch (left anterior descending branch) was taken, respectively. The myocardial tissue of the right ventricle (right coronary artery) and the posterior wall (circumflex branch) was sent for liquid chromatography-mass spectrometry to detect the distribution of tissue compounds. The specific steps are as follows: accurately weigh an appropriate amount of the analyte standard, prepare a 2.00 mg/mL stock solution with methanol for standby use, and mark it as S01. S01 was diluted with methanol to a series of concentration gradients of 5000 ng/ml, 2000 ng/mL, 500 ng/mL, 200 ng/mL, 50 ng/mL, and 20 ng/ml to obtain a standard curve. After weighing the above myocardial tissue samples, 1 mL of methanol solution was added, ground for 5 minutes, and centrifuged at 12000 rpm for 10 minutes. The supernatant was taken at 0.22 μm filter membrane filtration and sample analysis. The results showed that the standard curve of the compound showed a good linear relationship in the concentration range of 20~5000 ng/ml, $r^2>0.99$.

Figure 16:
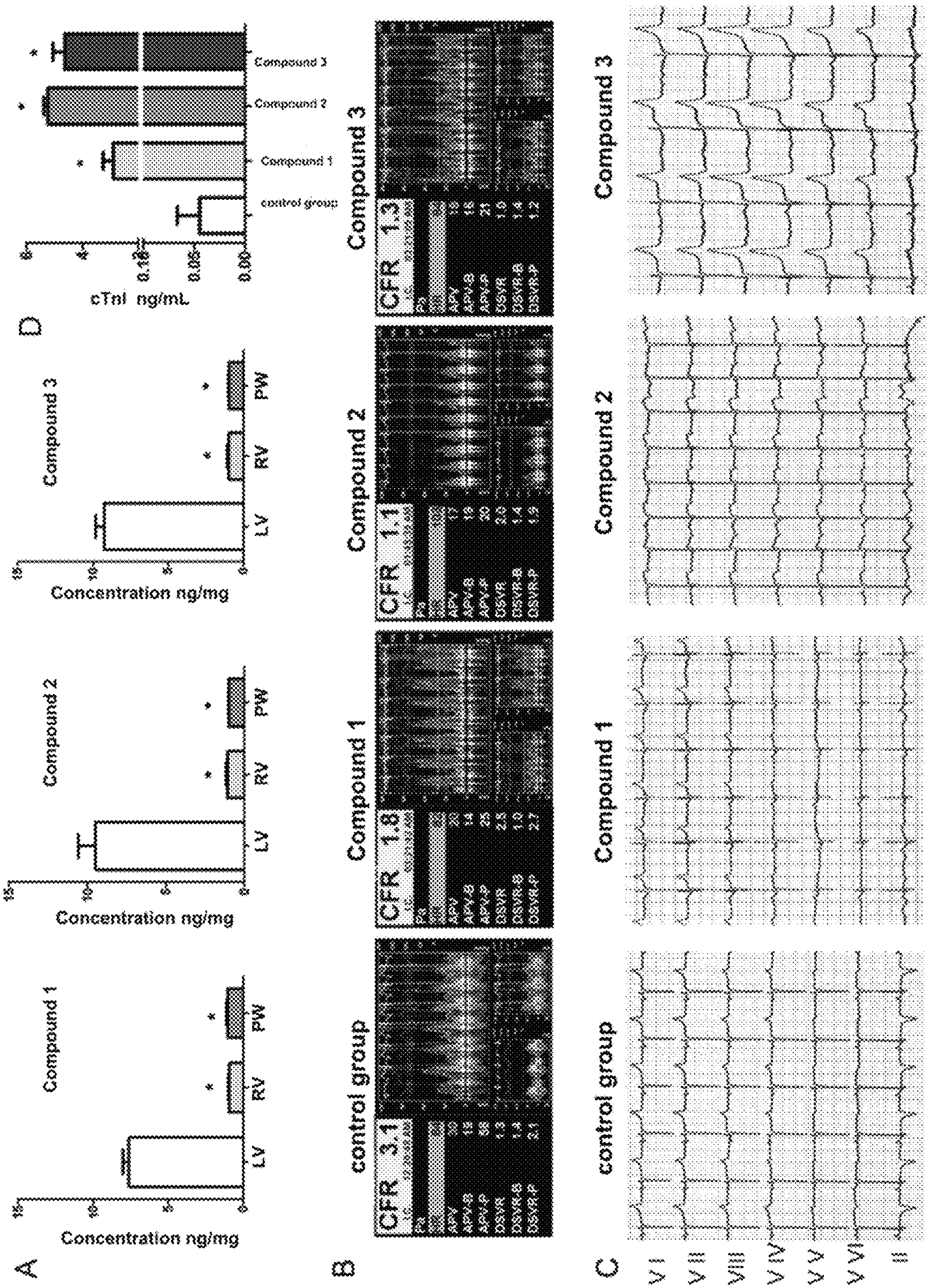
FIG. 16 shows directional distribution and biological effects of the ablation medium of the fluorobenzoyl anthracycline derivatives in the pig coronary artery via catheter intervention: determination of compound concentration in different target tissues (A), CFR determination of microcirculatory reserve (B), electrocardiogram (C) and myocardial ischemia index cTnI detection (D).

The above results show that: as shown in FIG. 16, the compounds of the invention have a high "first-pass effect" in local cardiac tissues, and show targeted distribution under catheter intervention, and the target concentration is 7 to 10 times that of non-targeted (FIG. 16, A). After targeted injection of Compounds 1, 2, and 3 of the invention, coronary blood flow was significantly slowed down, and the CFR data of the heart examination was ≤2.0 (FIG. 16, B), which indicates that the coronary blood flow reserve is reduced and microcirculatory blood supply is impaired; the precordial leads of the surface electrocardiogram show that the anthracene ring structure derivatives containing fluorinated benzoyl groups of the invention, especially Compounds 2 and 3, caused significant acute myocardial ischemia (FIG. 16, C). The blood cTnI increased significantly, confirming acute myocardial infarction (FIG. 16, D), and its effect was synchronized with the results of the electrocardiogram. The above results further confirmed that the endothelial apoptosis and necrosis of the micro-arteries of the experimental pigs occurred under the intervention of the compounds of the invention.

These experimental results comprehensively show that: the invention uses the anthracene ring structure derivative containing fluorinated benzoyl groups to derive the anthracene ring structure derivative containing fluorinated benzoyl groups as an ablation medium for heterogeneous myocardial chemical ablation, thereby achieving endothelial injury of cardiac arterioles, that is, controllable endothelial injury under precise tissue positioning. In constructing endothelial injury of cardiac arterioles under precise tissue positioning, the invention has a unique binary path; first, the anthracene ring structure derivative compound containing fluorinated benzoyl groups designed based on the lipophilic active group trifluoromethyl, with the help of interventional technology, produces an efficient "first-pass effect" on target cells under blood flow (the anthracene ring structure derivative containing fluorinated benzoyl groups is carried by arterial blood flow, and when the drug-carrying blood When the fluid flows through the tissue for the first time, the endothelium achieves efficient uptake and "bioavailability"); research data show that the distribution concentration of the anthracene ring structure derivative containing fluorinated benzoyl in the target tissue of the ablation medium of the invention can reach 7 to 10 times that of the non-target tissue. Secondly, the anthracene ring structure derivative containing fluorinated benzoyl interacts with the endothelium of the cardiac arterioles, producing a specific biochemical reaction, and through the cascade transduction of the derived molecular signals, the endothelial cells of the intramunal penetrating resistance arteries are targeted and damaged. The endothelial damage of the intramunal penetrating resistance arteries is a special self-controlled localized damage. It will cause arterial blood flow attenuation and conditional myocardial ischemia, thereby achieving the ablation medium at an effective concentration to induce severe apoptosis of the arteriolar endothelium in the intervention target area, and ultimately lead to myocardial ischemia and necrosis.

Briefly, this invention discloses the fluorobenzoyl anthracycline derivatives with superior efficacy in myocardial ablation, combining targeted delivery, controlled endothelial damage, and safe application through catheter-based interventions. The derivatives demonstrate a "dual-pathway" mechanism: lipid group-driven first-pass uptake and biochemical endothelial targeting. Microvascular damage results from the interaction between derivatives and endothelial cells of intramunal penetrating resistance arteries, leading to regional myocardial ischemia and tissue necrosis.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

What is claimed is:

1. A method of preparing a class of fluorobenzoyl anthracycline derivatives, comprising:

reacting an anthracycline compound represented by Formula (1) or its hydrochloride, Formula (1)

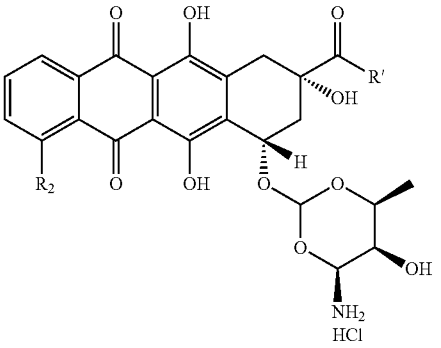

with a trifluoromethyl-substituted benzoyl chloride represented by Formula (2),

Formula (2)

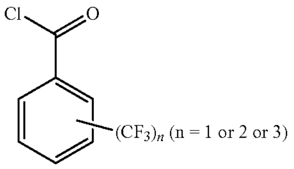

to yield the following class of fluorobenzoyl anthracycline derivatives,

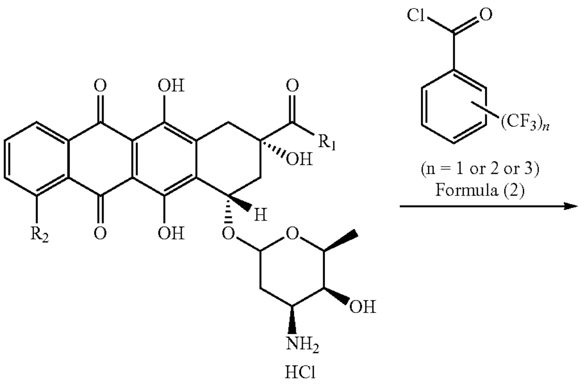

Formula (1)

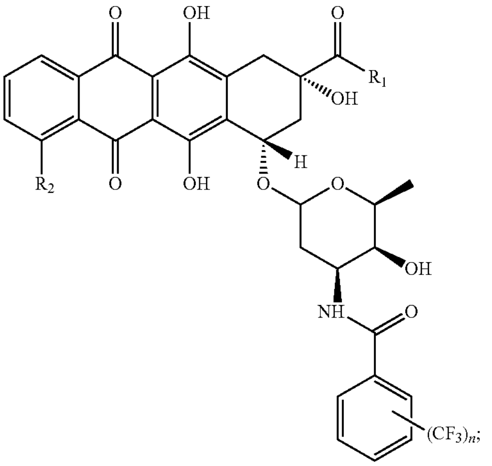

(n = 1 or 2 or 3)

or with a trifluoromethylphenyl-substituted benzoyl chloride represented by Formula (3), Formula (3)

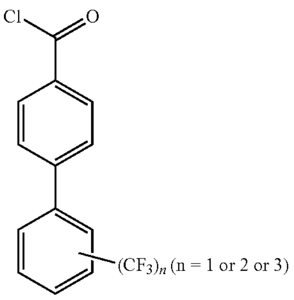

to yield the following class of fluorobenzoyl anthracycline derivatives,

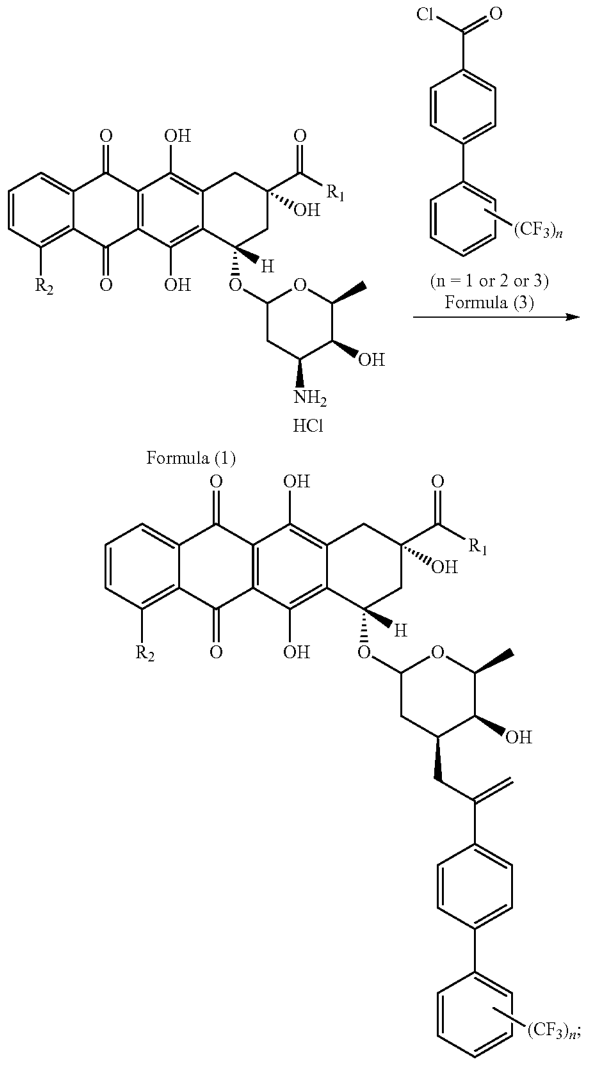

Formula (1)

(n = 1 or 2 or 3)

via an amide reaction, to prepare the fluorobenzoyl anthracycline derivatives, wherein $R_1$ is selected from the group consisting of —$CH_3$, —$CH_2OH$ and —O—$CH_3$ groups; and $R_2$ is selected from the group consisting of —H, —OH and —O—$CH_3$ groups.

2. The method of claim 1, wherein said reacting step comprises:

dissolving the compound represented by Formula (1) in an organic solvent;

adding an acid-binding agent including triethylamine; and dropwise adding the compound represented by Formula (2) or the compound represented by Formula (3) at low temperature to acylate the amino group to yield the fluorobenzoyl anthracycline derivatives.

3. The method of claim 1, wherein a synthesis route of the trifluoromethylphenyl-substituted benzoyl chloride represented by Formula (3) comprises:

using tetrakis (triphenylphosphine) palladium as a catalyst, sodium carbonate as a base, and a mixture of 1,4-dioxane and water as a reaction solvent, reacting 4-iodobenzoic acid with mono-, di- or tri-trifluoromethylphenylboronic acid via a SUZUKI coupling reaction to generate 4-mono-, di- or tri-trifluoromethylphenylbenzoic acid; and reacting the generated 4-mono-, di- or tri-trifluoromethylphenylbenzoic acid with thionyl chloride to obtain 4-mono-, di- or tri-trifluoromethylphenylbenzoyl chloride,

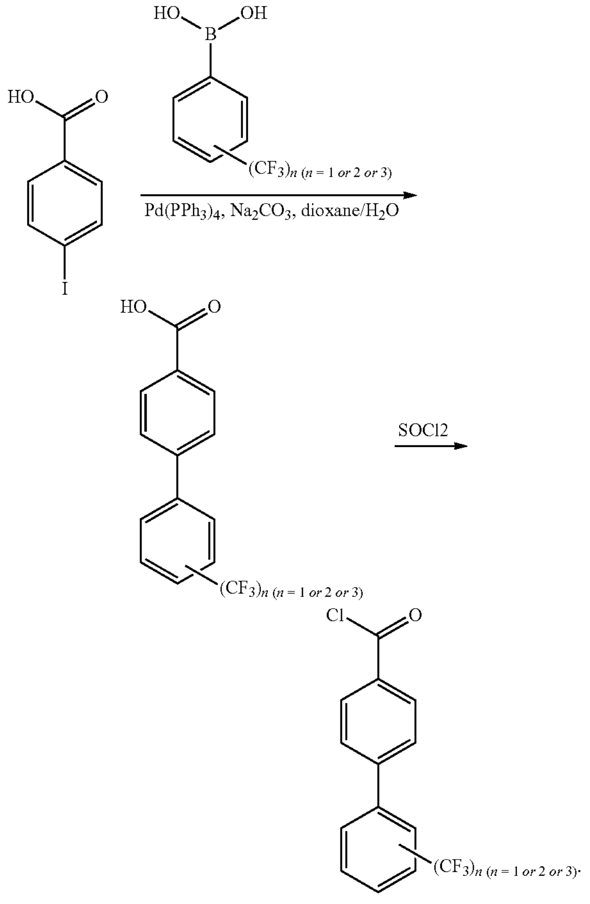

4. A class of fluorobenzoyl anthracycline derivatives, comprising:

a structure represented by formula (I):

Formula (II)

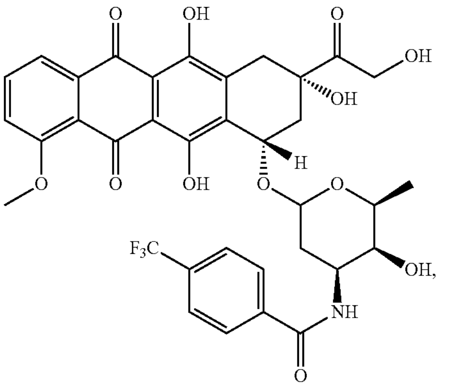

-continued

Formula (III)

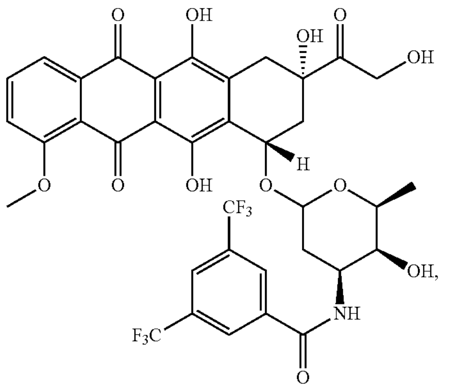

Formula (IV)

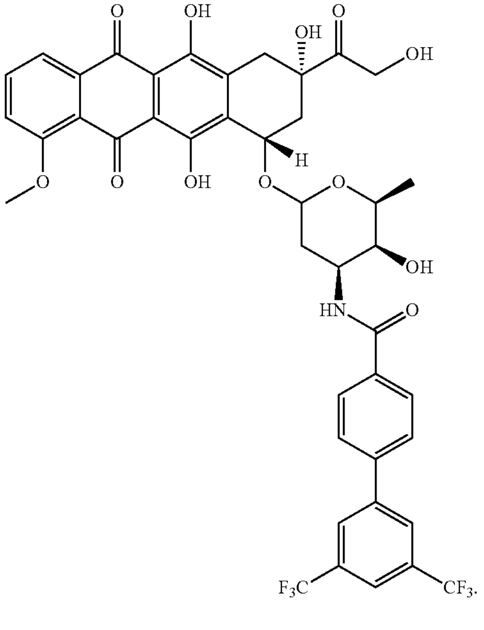

wherein $R_1$ is selected from the group consisting of $—CH_3$, $—CH_2OH$ and $—O—CH_3$ groups; $R_2$ is selected from the group consisting of —H, —OH and $—O—CH_3$ groups; and $R_3$ is a trifluoromethylphenyl-substituted benzoyl group, wherein the trifluoromethylphenyl-substituted benzoyl group comprises a mono-substituted, di-substituted, or tri-substituted trifluoromethylphenyl group having structures respectively shown as follows:

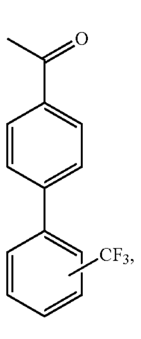

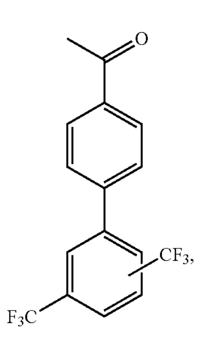

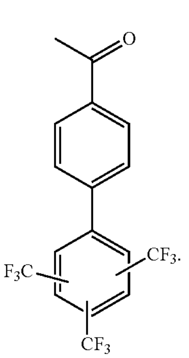

5. The class of fluorobenzoyl anthracycline derivatives of claim 4, wherein the trifluoromethylphenyl-substituted benzoyl group comprises one of followings structures:

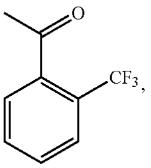

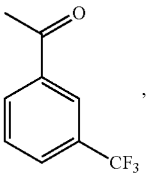

,

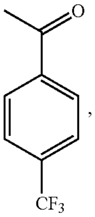

,

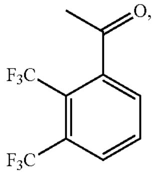

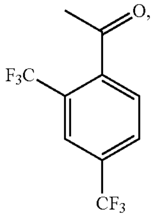

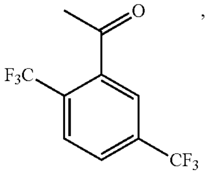

,

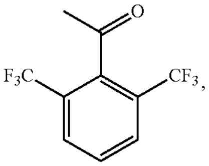

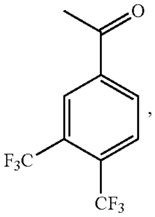

,

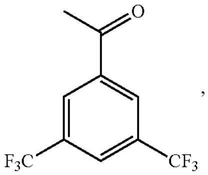

,

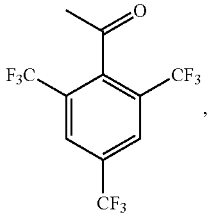

,

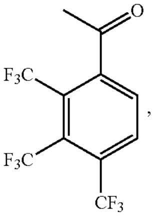

,

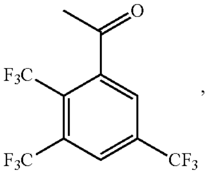

,

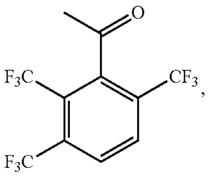

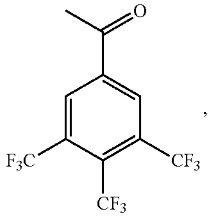

,

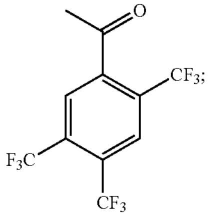

6. A fluorobenzoyl anthracycline derivative, comprising: a compound represented by formula:
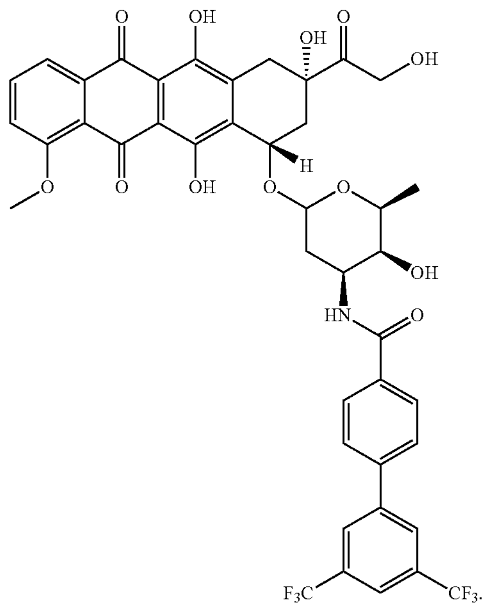
* * * * *